(12) United States Patent
Kaneko et al.

(10) Patent No.: US 11,261,200 B2
(45) Date of Patent: Mar. 1, 2022

(54) HETEROARYLTRIFLUOROBORATE COMPOUNDS FOR THE TREATMENT OF MYCOBACTERIAL INFECTIONS

(71) Applicant: The Global Alliance for TB Drug Development, Inc., New York, NY (US)

(72) Inventors: Takushi Kaneko, Guilford, CT (US); Nader Fotouhi, Basking Ridge, NJ (US)

(73) Assignee: The Global Alliance for TB Drug Development, Inc., New York, NY (US)

(*) Notice: Subject to any disclaimer, the term of this patent is extended or adjusted under 35 U.S.C. 154(b) by 0 days.

(21) Appl. No.: 16/335,326

(22) PCT Filed: Oct. 5, 2017

(86) PCT No.: PCT/US2017/055230
§ 371 (c)(1),
(2) Date: Mar. 21, 2019

(87) PCT Pub. No.: WO2018/067762
PCT Pub. Date: Apr. 12, 2018

(65) Prior Publication Data
US 2019/0276478 A1 Sep. 12, 2019

Related U.S. Application Data

(60) Provisional application No. 62/404,365, filed on Oct. 5, 2016.

(51) Int. Cl.
| | | |
|---|---|---|
| C07F 5/02 | (2006.01) | |
| A61P 31/06 | (2006.01) | |
| A61K 31/69 | (2006.01) | |
| A61K 45/06 | (2006.01) | |
| A61K 31/4409 | (2006.01) | |
| A61K 31/4965 | (2006.01) | |

(52) U.S. Cl.
CPC ............ *C07F 5/02* (2013.01); *A61K 31/4409* (2013.01); *A61K 31/4965* (2013.01); *A61K 31/69* (2013.01); *A61K 45/06* (2013.01); *A61P 31/06* (2018.01); *C07F 5/027* (2013.01)

(58) Field of Classification Search
CPC ...................................................... C07F 5/027
See application file for complete search history.

(56) References Cited

U.S. PATENT DOCUMENTS

| | | |
|---|---|---|
| 9,908,819 B1 | 3/2018 | Kollenberg |
| 2012/0065066 A1 | 3/2012 | Mathews et al. |
| 2015/0322092 A1 | 11/2015 | Chellappan et al. |

FOREIGN PATENT DOCUMENTS

| | | |
|---|---|---|
| KR | 20100082255 A | 7/2010 |
| KR | 20110026196 A | 3/2011 |
| WO | 2004056322 A2 | 7/2004 |
| WO | 2009/010488 A1 | 1/2009 |
| WO | 2013/014060 A1 | 1/2013 |
| WO | 2015085909 A1 | 6/2015 |
| WO | 2016097013 A1 | 6/2016 |

OTHER PUBLICATIONS

The International Search Report and Written Opinion, dated Feb. 5, 2018, in the related PCT Appl. No. PCT/US17/55230.
PUBCHEM CID 53397205, Create Date: Oct. 30, 2011 (Oct. 30, 2011) pp. 1-12.
Molander et al. "Organotrifluoroborates and Monocoordinated Palladium Complexes as Catalysts—A Perfect Combination for Suzuki-Miyaura Coupling", Angew Chem Int Ed Engl. 1, 7, 10, 16, 18, 19, 24-26 2009; vol. 48(49), pp. 9240-9261.
The extended European search report, dated Apr. 9, 2020, in the related European Patent Appl. No. 17859151.7.
Schimler et al: "Copper-Mediated Functionalization of ArylTrifluoroborates", SYNLETT, vol. 27, No. 15, Sep. 5, 2016, pp. 2279-2284, XP55680710.
Molander G A et al: "Palladium-Catalyzed Suzuki-Miyaura Cross-Coupling Reactions of Potassium Aryl- and Heteroaryltrifluoroborates", Journal of Organic Chemistry, American Chemical Society, US, vol. 68, No. 11, May 30, 2003 (May 30, 2003), pp. 4302-4314, XP001160394.
Nathalie Lecat-Guillet et al: "Discovery of Aryltrifluoroborates as Potent Sodium/Iodide Symporter (NIS) Inhibitors", CHEMMEDCHEM, vol. 3, No. 8, Aug. 18, 2008, pp. 1207-1209, XP55680771.
Marc Presset et al: "Copper-Mediated Radical Trifluoromethylation of Unsaturated Potassium Organotrifluoroborates", Journal of Organic Chemistry, vol. 78, No. 24, Dec. 20, 2013, pp. 12837-12843, XP55680755.
Guillaume Berionni et al: "Electrophilic Aromatic Substitutions of Aryltrifluoroborates with Retention of the BF 3-Group: Quantification of the Activating and Directing Effects of the Trifluoroborate Group", Journal of the American Chemical Society, vol. 135, No. 16, Apr. 24, 2013, pp. 6317-6324, XP55680795.
The English translation of the Eurasian Office Action, dated Aug. 24, 2020, in the related Eurasian Appl. No. 201992153/28.
The English translation of the Eurasian Office Action, dated Jan. 26, 2021, in the related Eurasian Appl. No. 201992153/28.
The English translation of the Chinese Office Action, dated Dec. 1, 2020, in the related Chinese Appl. No. 201780075198.1.

(Continued)

*Primary Examiner* — Emily A Bernhardt

(57) ABSTRACT

Provided herein are compounds of the formula (I): as well as pharmaceutically acceptable salts thereof, wherein the substituents are as those disclosed in the specification. These compounds, and the pharmaceutical compositions containing them, are useful for the treatment of tuberculosis.

20 Claims, 3 Drawing Sheets

(56) References Cited

OTHER PUBLICATIONS

The Indian Office Action, dated Nov. 25, 2020, in the related Indian Appl. No. 201917011441.

The English translation of the Japanese Office Action, dated Jul. 26, 2021, in the related Japanese Appl. No. 2019-518022.

Fontaine, F. et al., "First Identification of Boronic Species as Novel Potential Inhibitors of the *Staphylococcus aureus* NorA Efflux Pump," Journal of Medicinal Chemistry, USA, 2014, 57(6), pp. 2536-2548.

Molander, G. A. et al., "Nitrosation of Aryl and Heteroaryltrifluoroborates with Nitrosonium Tetrafluoroborate," Journal of Organic Chemistry, Apr. 24, 2012, 77(9), pp. 4402-4413.

Wilson, P. G. et al., "Suzuki-Miyaura Coupling Reactions of Iodo(difluoroenol) Derivatives, Fluorinated Building Blocks Accessible at Near-Ambient Temperatures," Journal of Organic Chemistry, USA, Jul. 9, 2012, 77(15), pp. 6384-6393.

Molander, G. A. et al., "Metal-Free Chlorodeboronation of Organotrifluoroborates," Journal of Organic Chemistry, Aug. 3, 2011, 76(17), pp. 7195-7203.

Noreen, M. et al., "Arylation and Heteroarylation of Thienylsulfonamides with Organotrifluoroborates," Journal of Organic Chemistry, Jul. 14, 2014, 79(15), pp. 7243-7249.

Molander, G. et al., Scope of the Suzuki-Miyaura Cross-Coupling Reactions of Potassium Heteroaryltrifluoroborates, Journal of Organic Chemistry, 2009, 74(3), pp. 973-980.

Molander, G. A. et al., "Oxidation of Organotrifluoroborates via Oxone," Journal of Organic Chemistry, 76(2), pp. 623-630, Dec. 30, 2010.

Registry(STN) [online], Entered STN: Oct. 11, 2010, Date of Retrieval: Jun. 9, 2021, CAS Registry No. 1245906-68-6.

Batey, R. A. et al., "Synthesis and cross-coupling reactions of tetraalkylammonium organotrifluoroborate salts," Tetrahedron Letters, 2001, 42(52), pp. 9099-9103.

Saurat, T. et al., "Design, Synthesis, and Biological Activity of Pyridopyrimidine Scaffolds as Novel PI3K/mTOR Dual Inhibitors," Journal of Medicinal Chemistry, 2014, 57(3), pp. 613-631.

Ren, W. et al., Palladium-catalyzed Suzuki-Miyaura cross-coupling reaction of potassium 2-pyridyl trifluoroborate with aryl (heteroaryl) halides, Tetrahedron, 2012, 68(5), pp. 1351-1358.

Registry (STN) [online], Entered STN: Jun. 5, 2012 or before, Date of Retrieval: Jun. 7, 2021, CAS Registry Nos. 1375328-10-1, 1333326-03-6, 1245906-67-5, 1245906-65-3, 1245906-64-2, 1245906-63-1, 1150654-92-4, 1150654-88-8, 1150654-85-5, 1150654-69-5, 1150654-62-8, 1073468-31-1.

HETEROARYLTRIFLUOROBORATE COMPOUNDS FOR THE TREATMENT OF MYCOBACTERIAL INFECTIONS

CROSS-REFERENCE TO RELATED APPLICATIONS

This application is a National Stage Application of PCT/US2017/055230 filed Oct. 5, 2017, which claims priority from U.S. Provisional Patent Application No. 62/404,365, filed on Oct. 5, 2016. The priority of both said PCT and U.S. Provisional Patent Application are claimed. Each of prior mentioned applications is hereby incorporated by reference herein in its entirety.

FIELD OF THE INVENTION

The invention is directed, for example, to compounds of formula (I):

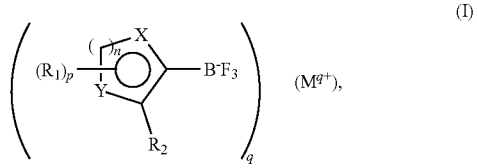

and to pharmaceutical compositions comprising the compounds. The compounds and compositions disclosed herein are antibacterials and are useful for the treatment of tuberculosis and other mycobacterial infections.

All documents cited or relied upon below are expressly incorporated herein by reference.

BACKGROUND OF THE INVENTION

*Mycobacterium tuberculosis* ("Mtb") is the causative agent of tuberculosis ("TB"), a devastating infectious disease. It is estimated that about 2 million TB patients die each year globally. Failure to properly treat tuberculosis has caused global drug resistance in Mtb and thus rendering some medications ineffective.

Pyrazinamide (PZA) is one of the four current first-line TB drugs. Its introduction in 1970s and 80s enabled the shortening of TB treatment from 9-12 months to 6 months. In spite of its importance, the mechanism of PZA is not well understood. But it is generally accepted that PZA is a prodrug that is converted by pyrazinamidase (PncA) in Mtb to active form pyrazinoic acid (POA). The minimum inhibitory concentration of PZA against Mtb is high under a standard culture conditions (>200 μM) and it shows up active when the culture medium pH is around 5. POA is theorized to acidify the cytoplasm of M tb, to disrupt the membrane potential of Mtb, and/or to affect the pantothenate and CoA syntheses (Y. Zhang, W. Shi, W. Zhang, D. Mitchison, 2014, Microbiol Spectr. 2(4):MGM2-0023-2013). A feature of PZA is that it is more effective against persistent Mtb rather than rapidly growing Mtb. The other characteristic feature of PZA is that it synergizes with other TB drugs as shown most dramatically with rifampicin or bedaquiline.

The effectiveness of PZA, however, has been reduced by the emergence of resistance. It is estimated that 16.2% of all TB cases are resistant to PZA whereas among the multi-drug resistant TB cases the number goes up to 60.5% (M. G. Whitfield, H. M. Soeters, R. M. Warren, T. York, S. L. Sampson, E. M. Streicher, P. D. van Helden, A. van Rie, 2015, PLoS One. 10(7):e0133869). The majority of PZA resistance is ascribed to mutations in PncA, the enzyme that converts PZA to POA.

A need exists in the art, therefore, to identify new chemical entities that can function like POA but can also overcome PZA resistance. Furthermore, it is desirable that such an agent have an increased safety margin and/or a more favorable PK profile compared to POA.

SUMMARY OF THE INVENTION

The present invention is directed to compounds of formula (I):

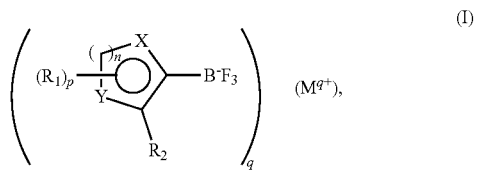

wherein:

X and Y, individually of each other, are C, N, O or S, with the provisos that X and Y are not both C, that X and Y are not both O or S when n is 2, and that X is O or S and Y is N when n is 1;

M is Ca, Cs, K, Li, Mg, Na or tetraalkyl ammonium ion $(R_3)_4N^+$;

$R_1$ is, individually in each occurrence, hydrogen, halogen, alkoxy, halo-alkoxy, lower alkyl, halo-lower alkyl, CN, —$(CH_2)_tCN$, —$NR_3R_4$, cycloalkyl, or heterocycloalkyl;

$R_2$ is hydrogen, halogen, alkoxy, halo-alkoxy, lower alkyl, halo-lower alkyl, CN, —$(CH_2)_tCN$, —$NR_3R_4$, cycloalkyl, or heterocycloalkyl;

$R_3$ and $R_4$, independently of each other, are hydrogen or lower alkyl; or $R_3$ and $R_4$, together with the nitrogen atom to which they are attached, combine to form a 4- to 7-membered ring;

n is 1 or 2;
p is 1 or 2;
q is 1 or 2; and
t is 1, 2, 3 or 4.

The present invention is also directed to compounds of formula II:

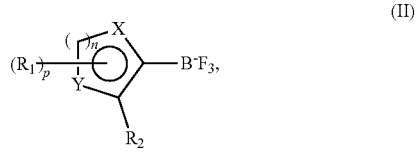

wherein:

X and Y, individually of each other, are C, N, O or S, with the provisos that X and Y are not both C, that X and Y are not both O or S when n is 2, and that X is O or S and Y is N when n is 1;

$R_1$ is $[(R_3)_3N^+]$— or $[(R_3)_3N^+(CH_2)_s]$—, with the proviso that $R_1$ is not $[(R_3)_3N^+]$— when n is 1;

$R_2$ is hydrogen, halogen, alkoxy, halo-alkoxy, lower alkyl or halo-lower alkyl;

each $R_3$ is, independently, lower alkyl, or two $R_3$'s together with the nitrogen to which they are attached form a 4 to 7-membered ring;

n is 1 or 2;

p is 1 or 2; and s is 1, 2, 3, 4, 5 or 6.

The present invention is also directed to pharmaceutical compositions containing the above compounds and to methods of treating microbial infections such as tuberculosis.

DETAILED DESCRIPTION OF THE INVENTION

Figure 1:
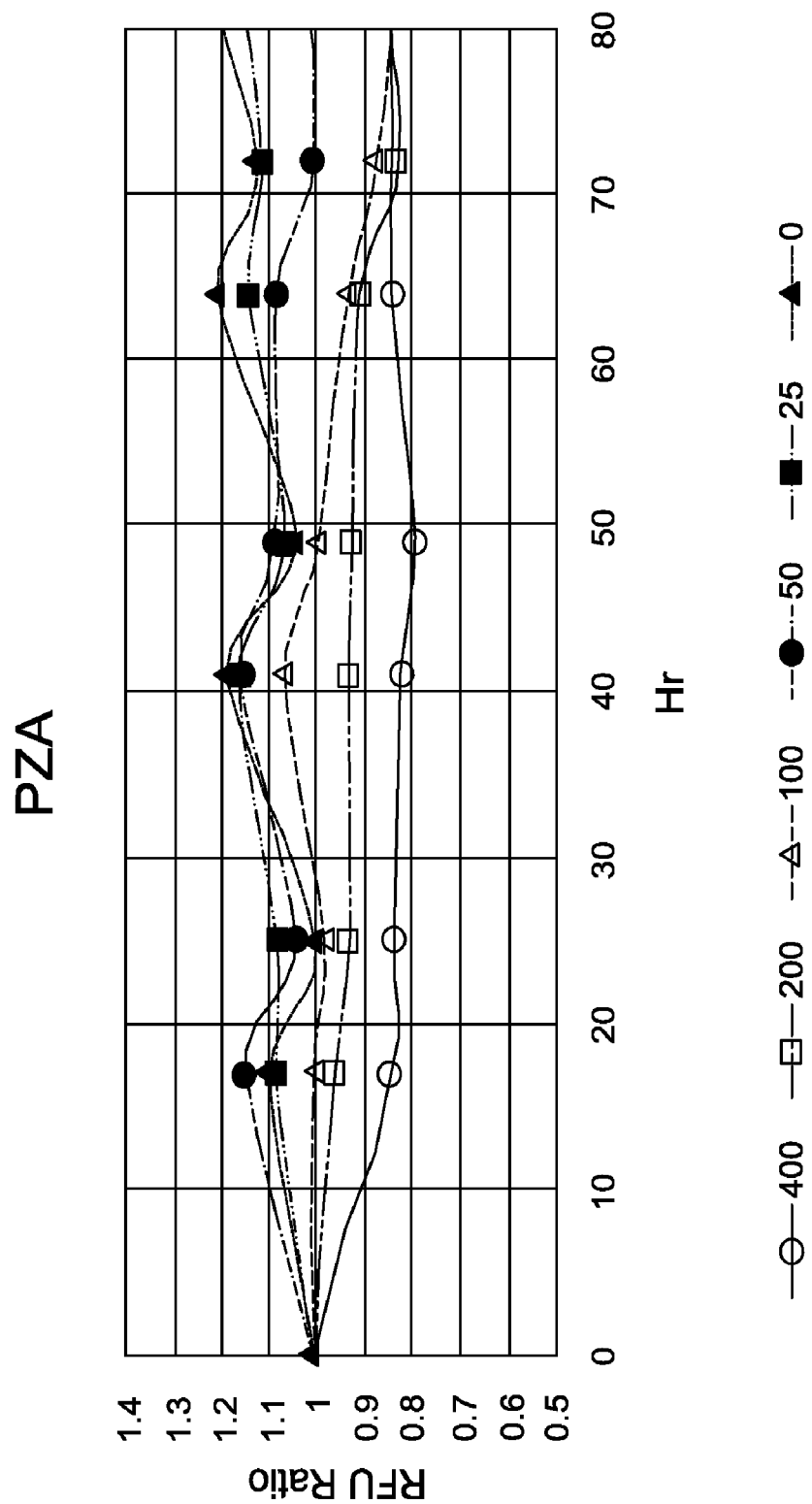
FIG. 1 shows the change in internal pH of Mtb when treated with PZA

It is to be understood that the terminology employed herein is for the purpose of describing particular embodiments, and is not intended to be limiting. Further, although any methods, devices and materials similar or equivalent to those described herein can be used in the practice or testing of the invention, certain methods, devices and materials are now described.

The present invention relates to novel heteroaryltrifluoroborate salts, their preparations, and to their use as drugs for treating tuberculosis and other mycobacteria infections, either alone or in combination with other anti-TB agents. The anti-TB agents include, but are not limited to, rifampicin, rifabutin, rifapentene, isoniazid, ethambutol, kanamycin, amikacin, capreomycin, clofazimine, cycloserine, para-aminosalicylic acid, linezolid, sutezolid, bedaquiline, delamanid, pretomanid, moxifloxacin, and levofloxacin.

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

As used herein, the term "alkenyl", alone or in combination with other groups, refers to a straight-chain or branched hydrocarbon residue having an olefinic bond.

The term "cycloalkyl" refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, norbornyl, adamantyl, indanyl and the like. In a preferred embodiment, the "cycloalkyl" moieties can optionally be substituted with one, two, three or four substituents. Each substituent can independently be alkyl, alkoxy, halogen, amino, hydroxyl or oxygen unless otherwise specifically indicated. Examples of cycloalkyl moieties include, but are not limited to, optionally substituted cyclopropyl, optionally substituted cyclobutyl, optionally substituted cyclopentyl, optionally substituted cyclopentenyl, optionally substituted cyclohexyl, optionally substituted cyclohexylene, optionally substituted cycloheptyl, and the like or those which are specifically exemplified herein.

The term "heterocycloalkyl" denotes a mono- or polycyclic alkyl ring, wherein one, two or three of the carbon ring atoms is replaced by a heteroatom such as N, O or S. Examples of heterocycloalkyl groups include, but are not limited to, morpholinyl, thiomorpholinyl, piperazinyl, piperidinyl, pyrrolidinyl, tetrahydropyranyl, tetrahydrofuranyl, 1,3-dioxanyl and the like. The heterocycloalkyl groups may be unsubstituted or substituted and attachment may be through their carbon frame or through their heteroatom(s) where appropriate.

The term "lower alkyl", alone or in combination with other groups, refers to a branched or straight-chain alkyl radical of one to nine carbon atoms, preferably one to six carbon atoms, more preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "aryl" refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthyl, 1,2-dihydronaphthyl, indanyl, 1H-indenyl and the like.

The alkyl, lower alkyl and aryl groups may be substituted or unsubstituted. When substituted, there will generally be, for example, 1 to 4 substituents present. These substituents may optionally form a ring with the alkyl, lower alkyl or aryl group with which they are connected. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl, more preferably, for example, methoxy and ethoxy), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, aryl sulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The term "heteroaryl," refers to an aromatic mono- or polycyclic radical of 5 to 12 atoms having at least one aromatic ring containing one, two, or three ring heteroatoms selected from N, O, and S, with the remaining ring atoms being C. Examples of such groups include, but not limited to, pyridinyl, pyrazinyl, pyridazinyl, 1,2,3-triazinyl, 1,2,4-triazinyl, oxazolyl, thiazolyl, and the like.

The heteroaryl group described above may be substituted independently with one, two, or three substituents. Substituents may include, for example: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono- or di-alkylaminocarbonylalkyl, arylaminocarbonyl), carbamates (e.g. alkoxycarbonylamino, aryloxycarbonylamino, aminocarbonyloxy, mono- or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkyl sulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more heteroatoms, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, piperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl, benzothiazoyl and carbolinyl).

As used herein, the term "alkoxy" means alkyl-O—; and "alkoyl" means alkyl-CO—. Alkoxy substituent groups or alkoxy-containing substituent groups may be substituted by, for example, one or more alkyl or halo groups.

As used herein, the term "halogen" means a fluorine, chlorine, bromine or iodine radical, preferably a fluorine, chlorine or bromine radical.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

In the practice of the method of the present invention, an effective amount of any one of the compounds of this invention, or a combination of any of the compounds of this invention, is administered via any of the usual and acceptable methods known in the art, either singly or in combination. The compounds or compositions can thus be administered, for example, ocularly, orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases. Thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are representative liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. In one embodiment, the therapeutically effective amount is in an amount of from about 10 mg to about 500 mg per day.

It will be appreciated, that the compounds of general formula I and II in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

Compounds of the present invention can be prepared beginning with commercially available starting materials and utilizing general synthetic techniques and procedures known to those skilled in the art. Chemicals may be purchased from companies such, as for example, Aldrich, Argonaut Technologies, VWR and Lancaster. Chromatography supplies and equipment may be purchased from such companies as for example AnaLogix, Inc, Burlington, Wis.; Biotage AB, Charlottesville, Va.; Analytical Sales and Services, Inc., Pompton Plains, N.J.; Teledyne Isco, Lincoln, Nebr.; VWR International, Bridgeport, N.J.; Varian Inc., Palo Alto, Calif., and Multigram II Mettler Toledo Instrument Newark, Del. Biotage, ISCO and Analogix columns are pre-packed silica gel columns used in standard chromatography.

The compounds of formula I can be prepared according to the following Schemes. These organotrifluoroborate salts can be prepared by several standard methods represented by a method of E. Vedejs, R. W. Chapman, S. C. Fields, S. Lin, and M. R. Scrimpf, *J. Org. Chem.* 1995, 60, 3020-3027, but more conveniently by a recent method of J. J. Lennox and G. C. Llyod-Jones, *Angew. Chem. Int. Ed.,* 2012, 51, 9385-9388.

Scheme 1

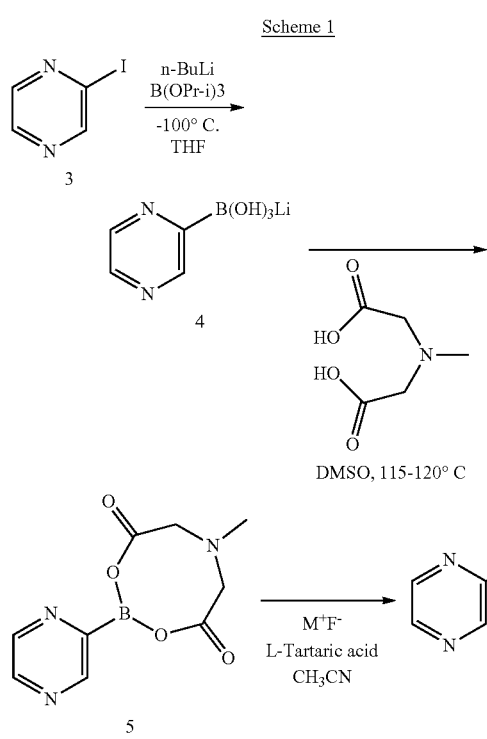

Scheme 2

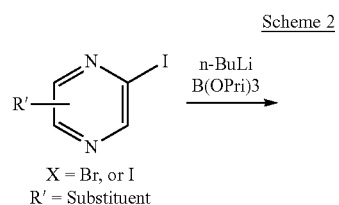

X = Br, or I
R′ = Substituent

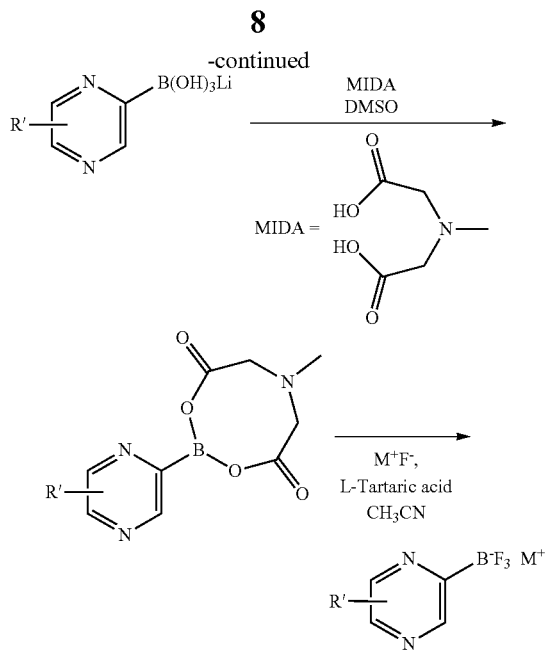

Scheme 3

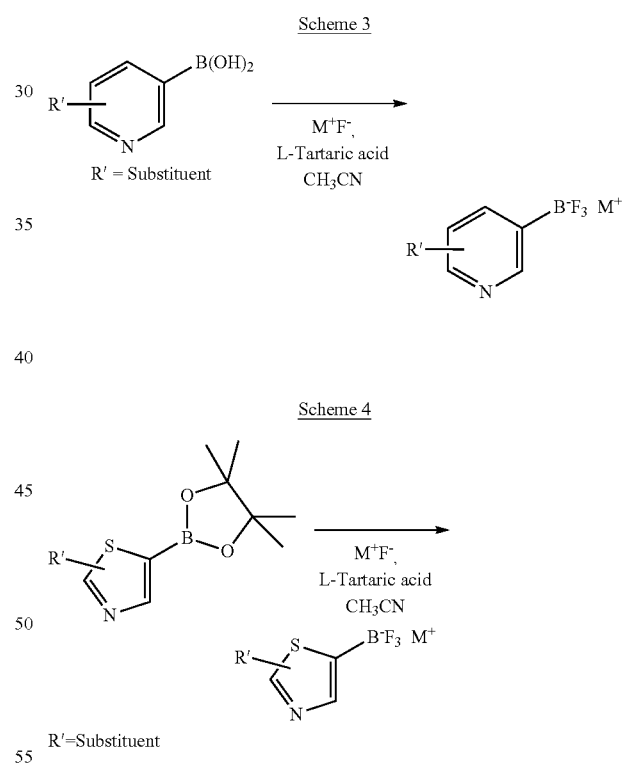

Representative compounds of the invention made by the methods described in the Schemes above and the Examples below are provided:

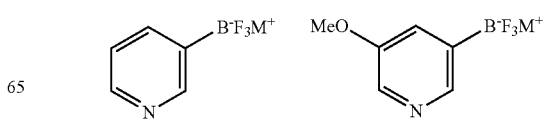

-continued

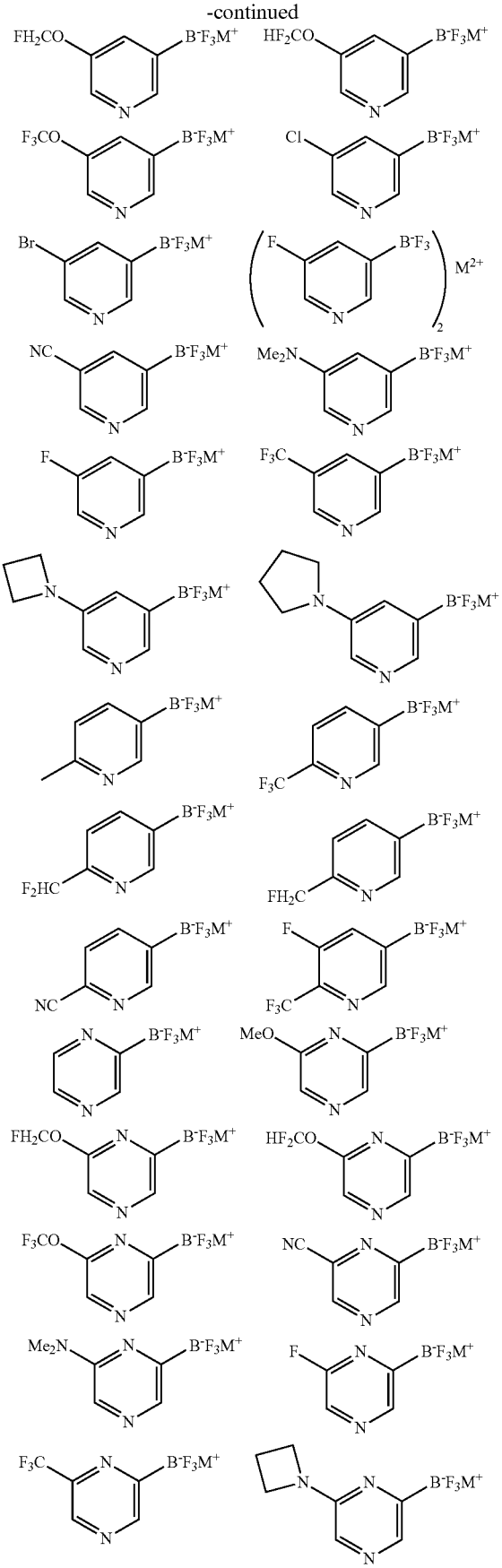
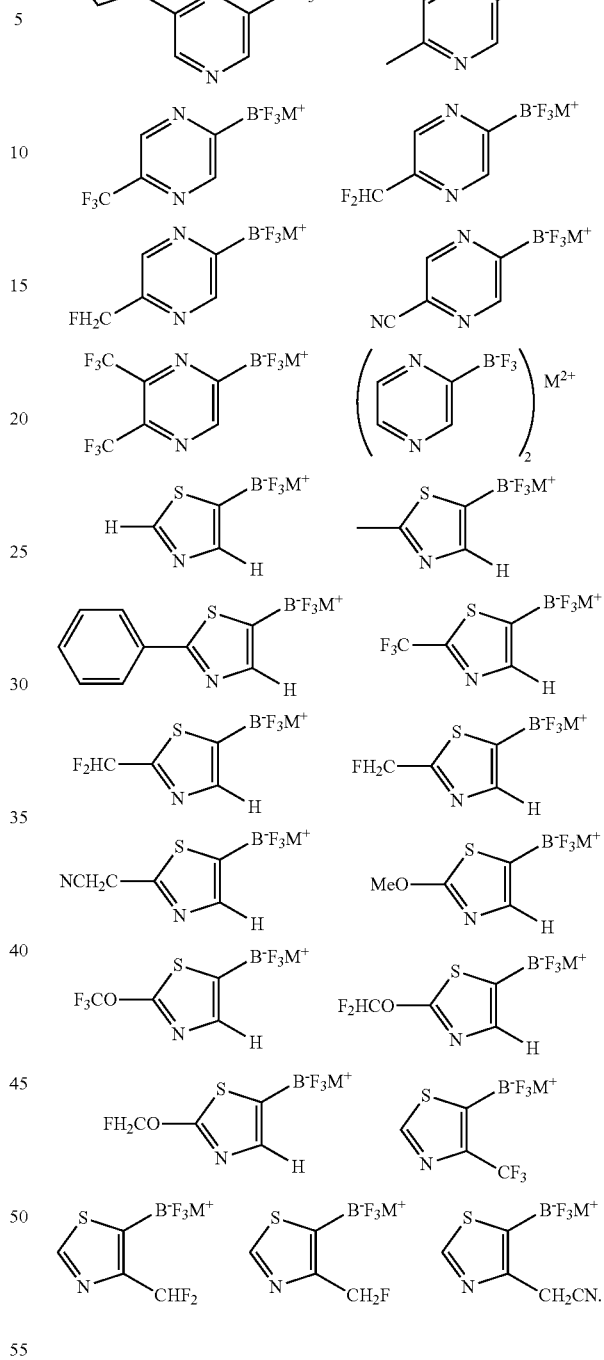

EXAMPLES

Synthetic methods for preparing the representative compounds of the present invention are illustrated in the following Examples. Starting materials are commercially available or may be made according to procedures known in the art or as illustrated herein. The following Examples are intended to help illustrate the invention, and are not intended to, nor should they be constructed to limit its scope.

Example 1

Synthesis of [trifluoro(pyrazin-2-yl)-boranyl]potassium(1+)

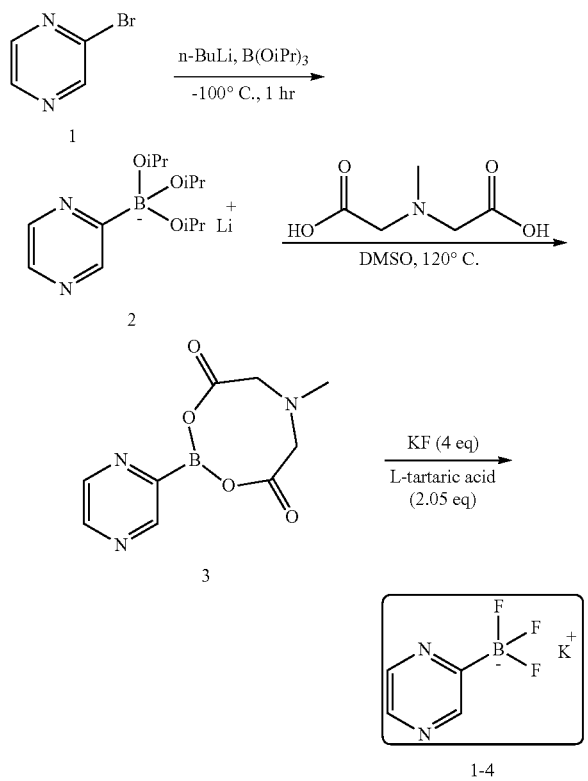

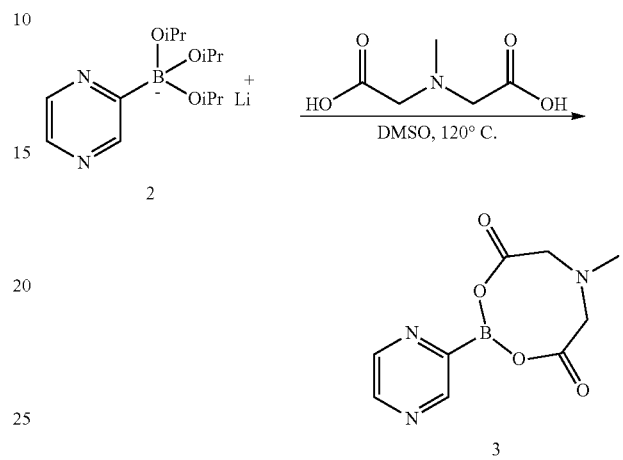

Synthesis of [trihydroxy(pyrazin-2-yl)-boranyl]lithium(1+)

Step 1. Synthesis of [triisopropoxy(pyrazin-2-yl)-boranyl]lithium(1+)

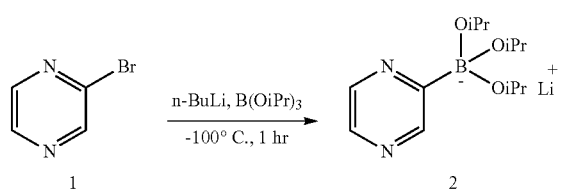

To a solution of 2-bromopyrazine (10 g, 62.90 mmol, 1 eq) and TRIISOPROPYL BORATE (13.28 g, 69.19 mmol, 16.23 mL, 98% purity, 1.1 eq) in THF (200 mL) was added n-BuLi (2.5 M in n-Hexane, 26.42 mL, 1.05 eq) drop-wise at 90° C. under $N_2$. During which, the temperature was maintained below 85° C. The reaction mixture was stirred at 85° C. for 20 min under $N_2$ atmosphere. TLC (Petroleum ether/Ethyl acetate=5:1) showed the starting material was consumed completely. The mixture was used directly in the next step. The crude product [triisopropoxy(pyrazin-2-yl)-boranyl]lithium(1+) (17.24 g, crude) in THF (200 mL) as a red-black solvent was used into the next step without further purification.

Step 2. Synthesis of 6-methyl-2-(pyrazin-2-yl)-1,3,6,2-dioxazaborocane-4,8-dione To a solution of 2-[carboxymethyl(methyl)amino]acetic acid (27.76 g, 188.70 mmol, 3 eq) in DMSO (160 mL) was added a solution of [triisopropoxy(pyrazin-2-yl)-boranyl]lithium(1+) (17.24 g, 62.90 mmol, 1 eq) in THF (200 mL) at 120° C. The mixture was stirred at 120° C. for 20 min. TLC indicated Reactant 2 was consumed completely and many new spots formed. The mixture was concentrated under reduced pressure. The residue was purified by column chromatography (SiO$_2$, Petroleum ether/Ethyl acetate/acetonitrile=3/1/0 to 0/10/1). The residue was washed with EtOAc (30 mL) and filtered. The filter cake was dried and washed with Acetonitrile (200 mL×3), filtered. The filtrate was concentrated under reduced pressure to give 6-methyl-2-(pyrazin-2-yl)-1,3,6,2-dioxazaborocane-4,8-dione (14.2 g) as a white solid.

$^1$H NMR (400 MHz, ACETONITRILE-d3) 8.81 (d, J=1.8 Hz, 1H), 8.73-8.68 (m, 1H), 8.56 (d, J=2.6 Hz, 1H), 4.20-4.13 (m, 2H), 4.05-3.98 (m, 2H), 2.62 (s, 3H)

Step 3. Synthesis of potassium trifluoro(pyrazin-2-yl)borate

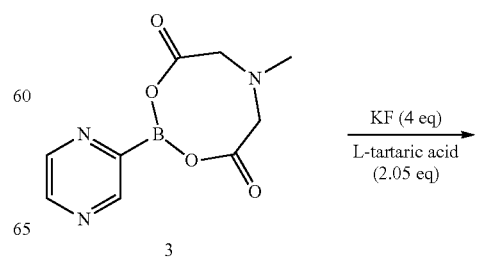

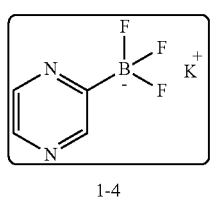

1-4

To a solution of 6-methyl-2-pyrazin-2-yl-1,3,6,2-dioxaza-borocane-4,8-dione (13.7 g, 58.30 mmol, 1 eq) in MeCN (233 mL) was added KF (10 M in water, 23.32 mL, 4 eq) and a solution of TARTARIC ACID (17.94 g, 119.51 mmol, 2.05 eq) in THF (90 mL). The mixture was stirred at 25° C. for 12 hr. TLC indicated Reactant 3 was consumed completely and one new spot formed. The mixture was filtered and the filtrate was concentrated under reduced pressure. The residue was washed with MeCN (50 mL) and filtered. The filter cake was dried to give the product. Compound potassium trifluoro(pyrazin-2-yl)borate (6 g, 32.26 mmol, 55.34% yield) was obtained as a white solid.

Re-Crystallization: 1-4

The desired product was dissolved with CH$_3$CN (1 g/40 mL) and warmed to 90° C. for 10 min. Then the hot suspension was filtered and the filtrate was concentrated under reduced pressure to remove most of CH$_3$CN. The suspension was filtered and the filter cake was washed with CH$_3$CN (10 mL) to give a white solid. The above procedure was repeated several times until good quality reached.

LCMS (ESI) m/z 146.8 [MK]$^-$ $^1$H NMR (400 MHz, ACETONITRILE-d3) 9.16 (s, 1H), 8.92 (d, J=3.2 Hz, 1H), 8.53 (dd, 3.1 Hz, 1H)

$^{19}$F NMR (400 MHz, ACETONITRILE-d3) -145.6 (q, 3F)

$^{11}$B NMR (400 MHz, ACETONITRILE-d3) 0.95 (q, 1B)

$^{13}$C NMR (101 MHz, ACETONITRILE-d3) 152.92 (br s, 1C), 146.42, 132.86 (br s, 1C)

Example 2

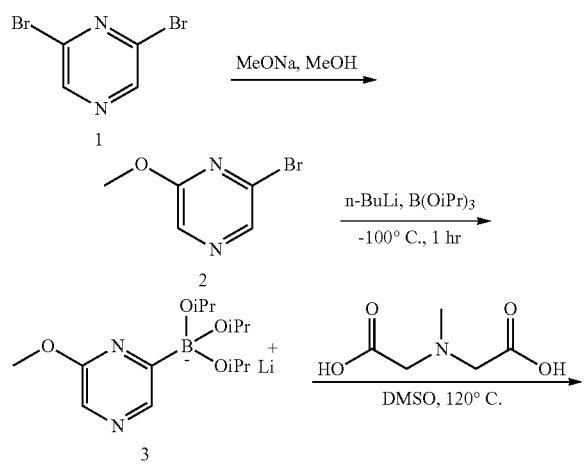

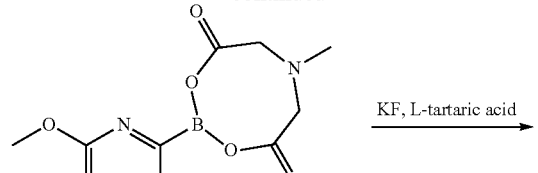

Step 1. Synthesis of 2-bromo-6-methoxy-pyrazine

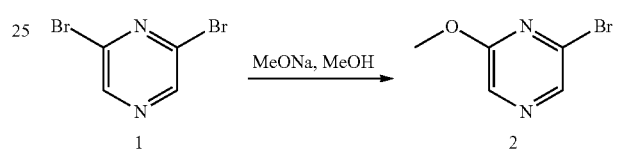

To a solution of 2,6-dibromopyrazine (67 g, 281.65 mmol, 1.00 eq) in MeOH (670 mL) was added NaOMe (18.26 g, 337.99 mmol, 1.2 eq). The mixture was stirred at 40° C. for 1 hr. LCMS showed ~99% of desired compound. The reaction mixture was quenched by addition of sat. NH$_4$Cl (80 mL), and concentrated under reduced pressure to give a solution (200 mL), and then diluted with H$_2$O 200 mL, extracted with EtOAc (200 mL×3). The combined organic layers were dried over anhydrous Na$_2$SO$_4$, filtered and concentrated under reduced pressure to give a residue. The residue was purified by column chromatography (SiO$_2$, Petroleum ether:Ethyl acetate=1:0 to 20:1). Compound 2-bromo-6-methoxy-pyrazine (45 g, 214.27 mmol, 76.08% yield, 90% purity) was obtained as a white solid.

LCMS (ESI) m/z 188.9 [M+H]$^+$ $^1$H NMR (400 MHz, DMSO) 8.39 (s, 1H), 8.34 (s, 1H), 3.91 (s, 3H)

Step 2. Synthesis of [triisopropoxy-(6-methoxy-pyrazin-2-yl)-boranyl]lithium(1+)

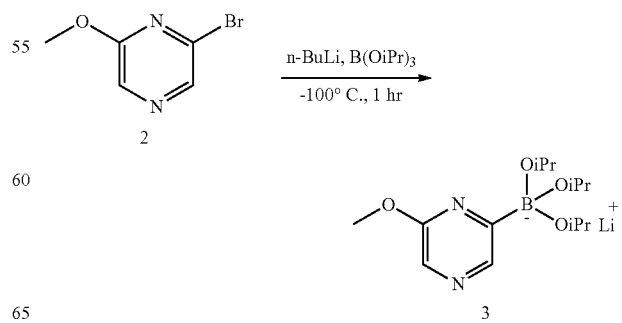

To a solution of 2-bromo-6-methoxy-pyrazine (20 g, 105.81 mmol, 1.00 eq) in THF (200 mL) was added TRI-ISOPROPYLBORATE (23.88 g, 126.98 mmol, 29.19 mL, 1.20 eq), n-BuLi (2.5 M in n-hexane, 50.79 mL, 1.2 eq) dropwise at 100° C. under N$_2$. The mixture was stirred at 100° C. for 1 hr. TLC indicated the starting material was consumed completely. The crude product [triisopropoxy-(6-methoxypyrazin-2-yl)-boranyl]lithium(1+) (32 g, crude) in THF (200 mL) was used into the next step without further purification. 1 mL of the reaction mixture was added to 5 mL MeOH. The mixture was concentrated in reduced pressure. $^1$H NMR showed the desired product.

$^1$H NMR (400 MHz, CD3CN) 8.15 (s, 1H), 7.88 (s, 1H), 3.90 (s, 3H)

Step 3. Synthesis of 2-(6-methoxypyrazin-2-yl)-6-methyl-1,3,6,2-dioxazaborocane-4,8-dione

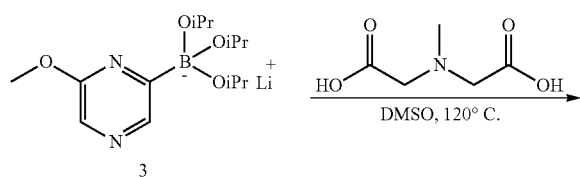

To a solution of 2-[carboxymethyl(methyl)amino]acetic acid (23.22 g, 157.83 mmol, 1.50 eq) in DMSO (190 mL) was added a solution of [triisopropoxy-(6-methoxypyrazin-2-yl)-boranyl] lithium(1+) (32 g, 105.22 mmol, 1 eq) in THF(200 mL) dropwise at 120° C. The mixture was stirred at 120° C. for 1 hour. TLC indicated the starting material was consumed completely and new spots formed. The mixture was concentrated under reduced pressure. The residue was purified by column chromatography (SiO$_2$, Petroleum ether:Ethyl acetate=5:1 to 0:1, Ethyl acetate:MeCN=5:1). Compound 2-(6-methoxypyrazin-2-yl)-6-methyl-1,3,6,2-dioxazaborocane-4,8-dione (16 g, 57.35 mmol, 54.51% yield, 95% purity) was obtained as a white solid.

$^1$H NMR (400 MHz, CD3CN) 8.33 (s, 1H), 8.17 (s, 1H), 4.16-4.10 (d, J=16.8 Hz, 2H), 4.04-3.98 (d, J=16.8 Hz, 2H), 3.89 (s, 3H), 2.65 (s, 3H)

Step 4. Synthesis of [trifluoro-(6-methoxypyrazin-2-yl)-boranyl]potassium(1+)

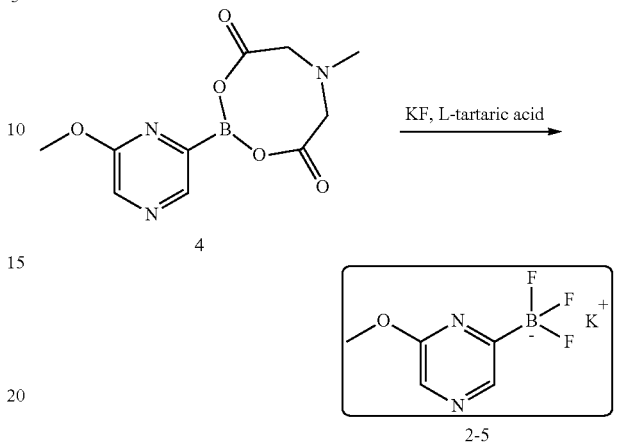

To a solution of 2-(6-methoxypyrazin-2-yl)-6-methyl-1,3,6,2-dioxazaborocane-4,8-dione (31 g, 116.97 mmol, 1 eq) in MeCN (470 mL) was added a solution of KF (27.18 g, 467.87 mmol, 10.96 mL, 4 eq) in H$_2$O (47 mL) and a solution of L-tartaric acid (35.99 g, 239.78 mmol, 2.05 eq) in THF (176 mL). The mixture was stirred at 35° C. for 24 hr. TLC indicated the starting material was consumed completely. The mixture was filtered and the filtrate was concentrated under reduced pressure. The residue was diluted with MeCN (150 mL) and filtered. The filter cake was dried under reduced pressure to give the product. Compound [trifluoro-(6-methoxypyrazin-2-yl)-boranyl]potassium(1+) (25 g, crude) was obtained as a white solid.

Recrystallization Condition:

25 g of desired product was dissolved with CH$_3$CN (1000 mL) and warmed to 90° C. for 10 min. Then the solution mixture was filtered as soon as possible before cooled to room temperature. The filtrate was cooled to 25° C., and the crystals formed. Then the precipitate was filtered and the filter cake was collected and dried under reduced pressure to give a white crystals.

LCMS (ESI) m/z 159.0 [M-KF+H+]$^+$ $^1$H NMR (400 MHz, ACETONITRILE-d3) 8.13 (s, 1H), 7.92 (s, 1H), 3.93 (s, 3H)

$^{19}$F NMR (400 MHz, ACETONITRILE-d3)-142.5 (q, 3F)

$^{11}$B NMR (400 MHz, ACETONITRILE-d3) 2.45 (q, 1B)

Example 3

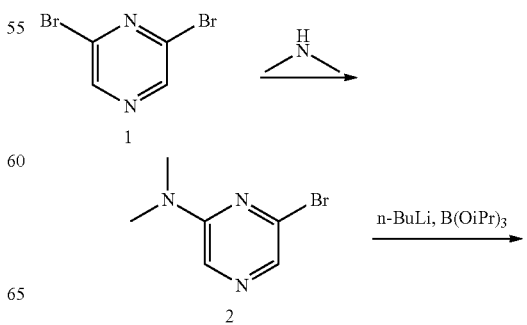

-continued

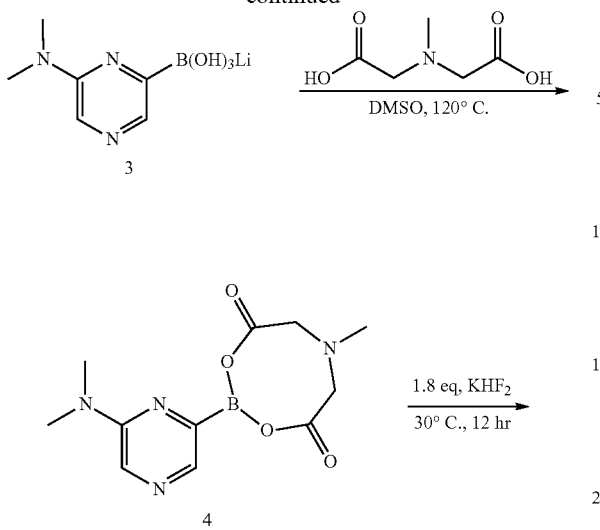

Step 1. Synthesis of 6-bromo-N,N-dimethylpyrazin-2-amine

The mixture of 2,6-dibromopyrazine (39.00 g, 163.95 mmol, 1.00 eq) and DIMETHYLAMINE (89.59 g, 655.80 mmol, 100.66 mL, 33% purity in water, 4.00 eq) was stirred at 20° C. for 3 hr. TLC indicated Reactant 1 was consumed completely and many new spots formed. The mixture was diluted with water (200 mL) and extracted with DCM (150 mL×3). The organic layer was dried over Na₂SO₄, filtered and concentrated under reduced pressure. The residue was purified by flash silica gel chromatography (ISCO®; 120 g SepaFlash® Silica Flash Column, Eluent of 0~15% Ethyl acetate/Petroleum ethergradient @ 85 mL/min). Compound 6-bromo-N,N-dimethyl-pyrazin-2-amine (33.00 g, 163.33 mmol, 99.62% yield) was obtained as a light yellow solid.

$^1$H NMR (400 MHz, CHLOROFORM-d) 7.88 (s, 1H), 7.85 (s, 1H), 3.12 (s, 6H)

Step 2. Synthesis of [6-(dimethylamino)pyrazin-2-yl]boronic acid; hydroxylithium

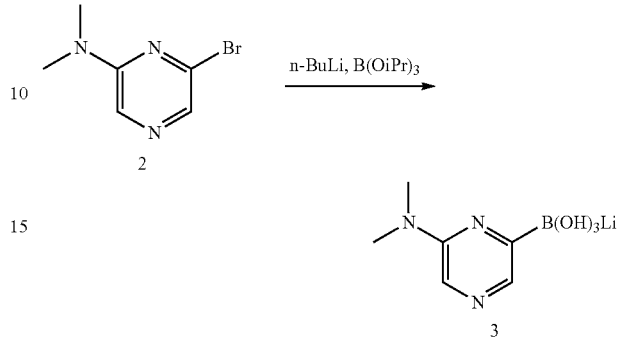

To a solution of 6-bromo-N,N-dimethyl-pyrazin-2-amine (9.90 g, 49.00 mmol, 1.00 eq) and TRIISOPROPYL BORATE (11.06 g, 58.80 mmol, 13.49 mL, 1.20 eq) in THF (100.00 mL) was added n-BuLi (2.5 M in n-hexane, 23.52 mL, 1.20 eq) dropwise at 100° C. The mixture was stirred at 100° C. for 1 hour. TLC indicated Reactant 2 was consumed completely. The crude product [6-(dimethylamino)pyrazin-2-yl] boronic acid; hydroxylithium (9.00 g, 47.14 mmol, 96.20% yield) in THF (100 mL) was used into the next step without further purification. 0.5 mL of the mixture was quenched by MeOH (2 mL) and concentrated under reduced pressure, which was confirmed by HNMR (ES5002-247-P1A).

$^1$H NMR (400 MHz, DEUTERIUM OXIDE) 7.72 (s, 1H), 7.64 (s, 1H), 2.88 (s, 6H)

Step 3. Synthesis of 2-(6-(dimethylamino)pyrazin-2-yl)-6-methyl-1,3,6,2-dioxazaborocane-4,8-dione

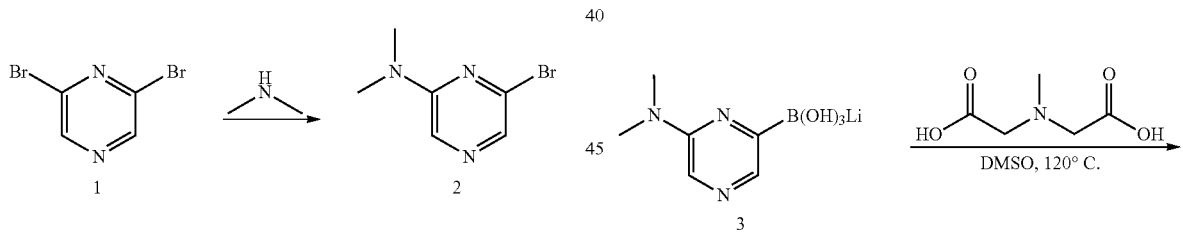

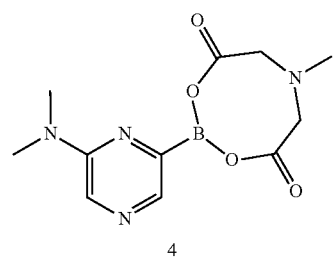

To a solution of 2-[carboxymethyl(methyl)amino]acetic acid (10.75 g, 73.07 mmol, 1.50 eq) in DMSO (100.00 mL) was added a solution of [6-(dimethylamino)pyrazin-2-yl] boronic acid ester; hydroxylithium (9.30 g, 48.71 mmol, 1.00 eq) in THF (100 mL) dropwise at 120° C. The mixture was stirred at 120° C. for 1 hour. TLC indicated Reactant 3 was consumed completely. The mixture was concentrated under reduced pressure. The residue was purified by column chromatography (SiO₂, Ethyl acetate/MeCN=1/0 to 10/1). Compound 2-[6-(dimethylamino)pyrazin-2-yl]-6-methyl-1,3,6,2-dioxazaborocane-4,8-dione (6.50 g, 23.38 mmol, 47.99% yield) was obtained as a white solid.

¹H NMR (400 MHz, ACETONITRILE-d3) 8.07 (s, 1H), 7.98 (s, 1H), 4.12 (d, J=16.8 Hz, 2H), 4.01 (d, J=16.8 Hz, 2H), 3.07 (s, 6H), 2.67 (s, 3H)

Step 4. Synthesis of potassium (6-(dimethylamino)pyrazin-2-yl)trifluoroborate

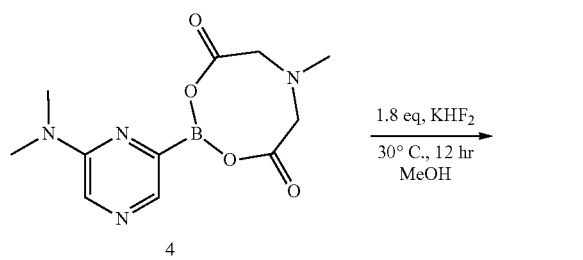

To a solution of 2-[6-(dimethylamino)pyrazin-2-yl]-6-methyl-1,3,6,2-dioxazaborocane-4,8-dione (6.00 g, 21.58 mmol, 1.00 eq) in MeOH (60.00 mL) was added KHF₂ (4.5 M in water, 8.63 mL, 1.80 eq). The mixture was stirred at 30° C. for 12 hour. TLC indicated ~10% of Reactant 4 was remained, and one major new spot with larger polarity was detected. The mixture was filtered and the filter cake was dried to give the product. Compound potassium; 6-difluoroboranyl-N,N-dimethyl-pyrazin-2-amine; fluoride (3.40 g, 14.84 mmol, 68.79% yield) was obtained as a light yellow solid.

LCMS (ESI) m/z 172.1 [MKF+H]⁺

¹H NMR (400 MHz, ACETONITRILE-d3) 8.25 (s, 1H), 7.91 (s, 1H), 3.19 (s, 6H)

¹⁹F NMR (377 MHz, ACETONITRILE-d3)-144.47 (br dd, J=43.5, 87.0 Hz, 3F)

¹¹B NMR (128 MHz, ACETONITRILE-d3) 2.10-0.40 (m, 1B)

Example 4

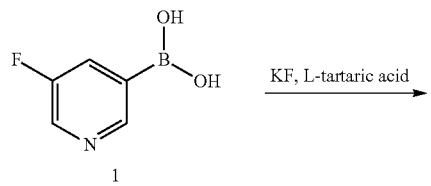

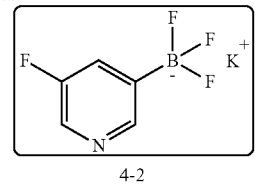

Step 1. Synthesis of [trifluoro-(5-fluoro-3-pyridyl)-boranyl] potassium(1+)

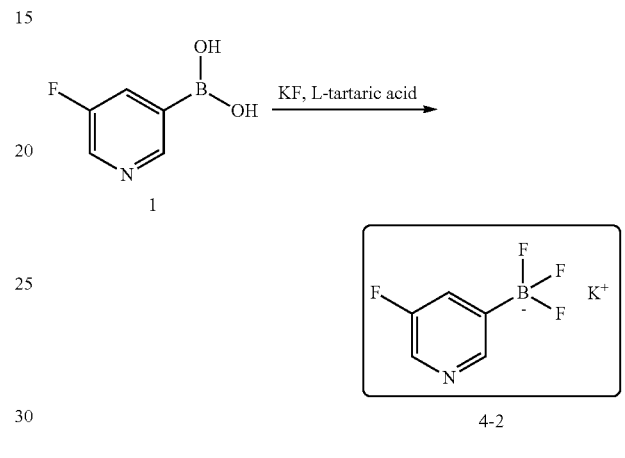

To a suspension of (5-fluoro-3-pyridyl)boronic acid (30 g, 212.90 mmol, 1 eq) in CH₃CN (851 mL) was added KF (49.48 g, 851.62 mmol, 4 eq) in H₂O (85.1 mL) at 18° C. The mixture was stirred until completely dissolved of the boronic acid, L-(+)-tartaric acid (65.51 g, 436.45 mmol, 2.05 eq) was dissolved into THF (319 mL) and added dropwise to the rapidly stirring biphasic mixture over a period of ten minutes. A white precipitate formed instantly and flocculated over a period of 2 hours. TLC showed the starting material was consumed. The mixture was filtered directly and the filter cake was washed with CH₃CN (100 mL). The filtrate was concentrated under reduced pressure to give a residue. The residue was recrystallized with CH₃CN (1 g/10 mL, 1 g/5 mL, 1 g/2.5 mL). Compound [trifluoro-(5-fluoro-3-pyridyl)-boranyl] potassium(1+) (15 g, 72.68 mmol, 34.14% yield, 98.35% purity) was obtained as a white solid.

LCMS (ESI) m/z 146.0 [MKF+H]⁺

¹H NMR (400 MHz, ACETONITRILE-d3) 8.43-8.36 (m, 1H), 8.20 (d, J=2.3 Hz, 1H), 7.51 (br d, J=8.4 Hz, 1H)

¹⁹F NMR (400 MHz, ACETONITRILE-d3)-130.5 (s, 1F), 141.5~143.0 (m, 3F)

¹¹B NMR (400 MHz, ACETONITRILE-d3) 1.5~3.5 (q, 1B)

Example 5

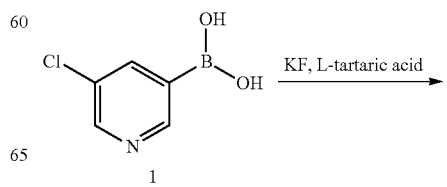

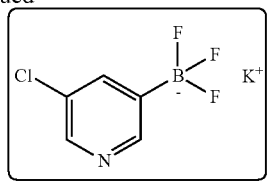

5-2

Step 1. Synthesis of [trifluoro-(5-fluoro-3-pyridyl)-boranyl] potassium(1+) ES5002-466-P1

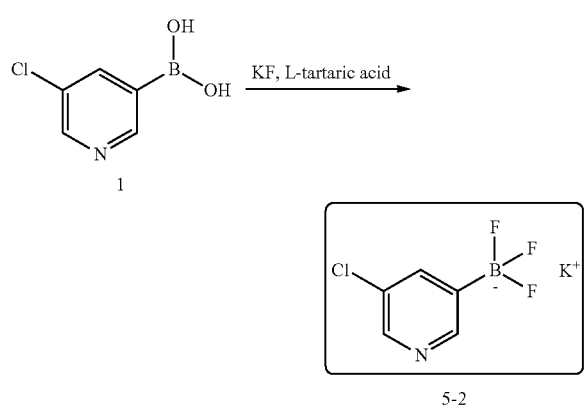

5-2

To a suspension of (5-chloro-3-pyridyl)boronic acid (20 g, 127.09 mmol, 1 eq) in CH₃CN (508 mL) was added KF (29.54 g, 508.38 mmol, 4 eq) in H₂O (51 mL) at 18° C. The mixture was stirred until complete dissolved of the boronic acid, L-(+)-tartaric acid (39.11 g, 260.54 mmol, 2.05 eq) was dissolved into THF (190 mL) and added dropwise to the rapidly stirring biphasic mixture over a period of ten minutes. A white precipitate formed instantly which flocculated over a period of 2 hours. TLC showed the starting material was consumed. The mixture was filtered directly and the filter cake was washed with CH₃CN (100 mL). The filtrate was concentrated under reduced pressure to give a residue. The residue was re-crystallized with CH₃CN (1 g/10 mL, 1 g/8 mL, 1 g/6 mL). Compound [(5-chloro-3-pyridyl)-trifluoro-boranyl] potassium(1+) (10 g, 45.57 mmol, 35.86% yield, 100% purity) was obtained as a white solid. LCMS (ESI) m/z 162.0 [M-KF+H]⁺

¹H NMR (400 MHz, ACETONITRILE-d3) 8.44 (s, 1H), 8.31 (s, 1H), 7.78 (s, 1H)

¹⁹F NMR (400 MHz, ACETONITRILE-d3)-142.5 (q, 3F)

¹¹B NMR (400 MHz, ACETONITRILE-d3) 1.5-4.5 (q, 1B)

Example 6

Scheme:

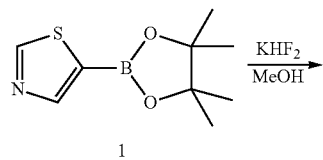

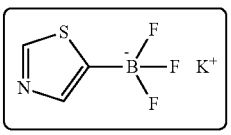

6-2

Step 1. Synthesis of potassium trifluoro(thiazol-5-yl)borate

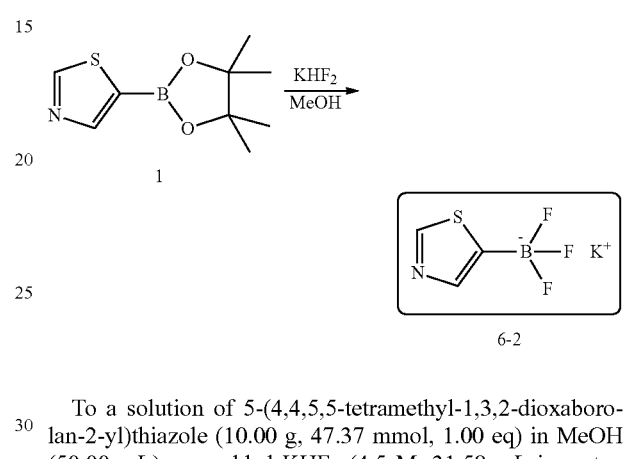

6-2

To a solution of 5-(4,4,5,5-tetramethyl-1,3,2-dioxaborolan-2-yl)thiazole (10.00 g, 47.37 mmol, 1.00 eq) in MeOH (50.00 mL) was added KHF₂ (4.5 M, 31.58 mL in water, 3.00 eq). The mixture was stirred at 25° C. for 3 hours. TLC indicated reactant 1 was consumed completely. The mixture was concentrated under reduced pressure. The mixture was washed with EtOAc (50 mL) and filtered. The filter cake was dried under reduced pressure to give the crude product. The crude product was washed with MeOH (20 mL) and filtered. The filtrate was concentrated under reduced pressure to afford compound potassium trifluoro(thiazol-5-yl)borate (2.95 g, 15.44 mmol, 32.60% yield, 100% purity) was obtained as a white solid.

MS (ESI) m/z 134.0 [MKF+H]⁺

¹H NMR (400 MHz, ACETONITRILE-d3) 8.73 (s, 1H), 7.67 (s, 3H)

¹⁹F NMR (377 MHz, ACETONITRILE-d3)-135.88 (br dd, J=44.8, 90.6 Hz, 3F)

¹¹B NMR (128 MHz, ACETONITRILE-d3) 1.86, 2.39 (q, J=45.9 Hz, 1B)

Example 7

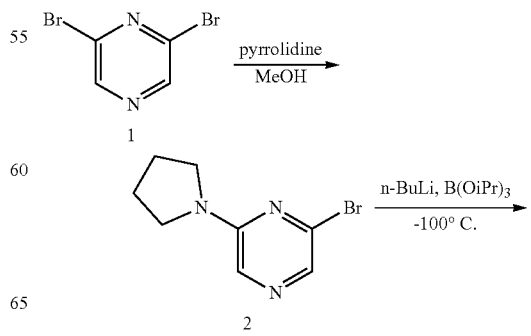

-continued

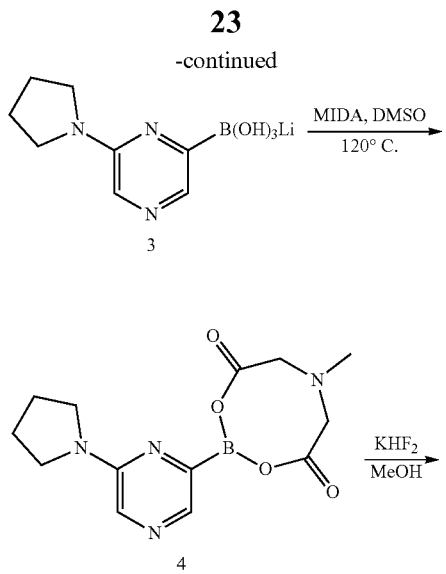

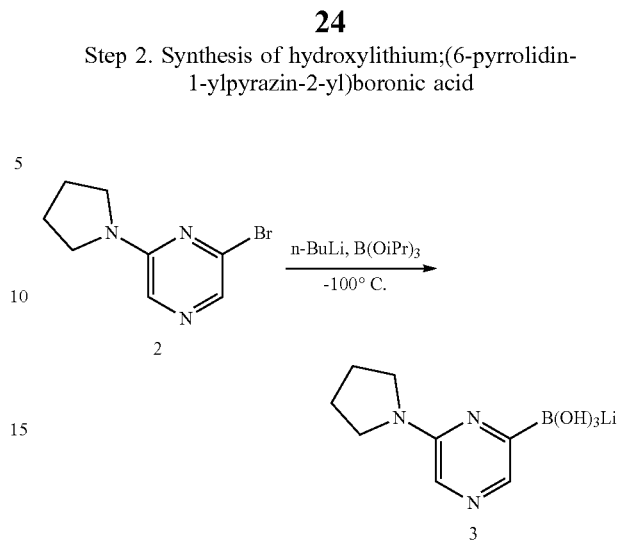

Step 2. Synthesis of hydroxylithium;(6-pyrrolidin-1-ylpyrazin-2-yl)boronic acid To a solution of 2-bromo-6-pyrrolidin-1-yl-pyrazine (1.90 g, 8.33 mmol, 1.00 eq) and TRIISOPROPYL BORATE (1.88 g, 10.00 mmol, 2.29 mL, 1.20 eq) in THF (25.00 mL) was added n-BuLi (2.5 M in n-hexane, 4.00 mL, 1.20 eq) at 100° C. dropwise. The mixture was stirred at 100° C. for 1 hour. TLC indicated reactant 2 was consumed completely. The crude product hydroxylithium;(6-pyrrolidin-1-ylpyrazin-2-yl)boronic acid (1.80 g, 8.30 mmol, 99.60% yield) in THF (20 mL) was used into the next step without further purification. 0.5 mL of the mixture was quenched with MeOH (2 mL), concentrated under reduced pressure and confirmed by HNMR.

$^1$H NMR (400 MHz, D$_2$O) 7.63 (s, 1H), 7.45 (s, 1H), 3.29-3.21 (m, 4H), 1.79 (br t, J=6.5 Hz, 4H)

Step 3. Synthesis of 6-methyl-2-(6-pyrrolidin-1-ylpyrazin-2-yl)-1,3,6,2-dioxazaborocane-4,8-dione

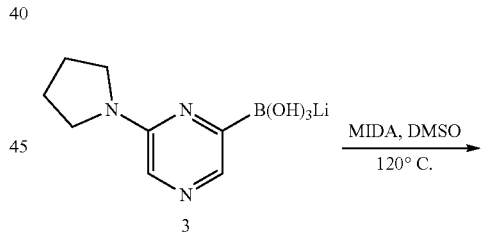

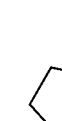

Step 1. Synthesis of 2-bromo-6-pyrrolidin-1-yl-pyrazine

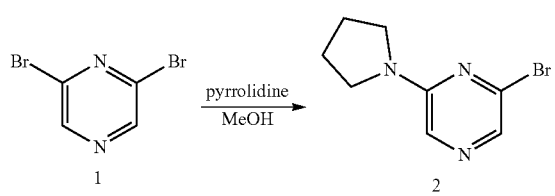 [SMILES: "MeOH" ; Brc1cncc(Br)n1 ; Brc1cncc(N2CCCC2)n1]

To a solution of 2,6-dibromopyrazine (2.00 g, 8.41 mmol, 1.00 eq) in MeOH (20.00 mL) was added pyrrolidine (1.79 g, 25.23 mmol, 2.11 mL, 3.00 eq). The mixture was stirred at 15° C. for 3 hour. TLC indicated reactant 1 was consumed completely. The mixture was quenched with water (50 mL) and extracted with DCM (50 mL×3). The organic layer was dried over Na$_2$SO$_4$, filtered and concentrated under reduced pressure. The residue was purified by flash silica gel chromatography (ISCO®; 24 g SepaFlash® Silica Flash Column, Eluent of 0-15% Ethyl acetate/Petroleum ethergradient @ 35 mL/min). Compound 2-bromo-6-pyrrolidin-1-yl-pyrazine (1.70 g, 7.45 mmol, 88.62% yield) was obtained as a white solid.

$^1$H NMR (400 MHz, CDCl$_3$) 7.82 (s, 1H), 7.73 (s, 1H), 3.48 (br t, J=6.5 Hz, 4H), 2.08-1.98 (m, 4H)

To a solution of 2-[carboxymethyl(methyl)amino]acetic acid ester (1.83 g, 12.45 mmol, 1.50 eq) in DMSO (20.00 mL) was added a solution of hydroxylithium;(6-pyrrolidin-1-ylpyrazin-2-yl)boronic acid (1.80 g, 8.30 mmol, 1.00 eq) in THF (20 mL) dropwise at 120° C. The mixture was stirred at 120° C. for 1 hr. TLC indicated reactant 3 was consumed completely. The mixture was concentrated under reduced pressure. The residue was purified by column chromatography (SiO$_2$, Ethyl acetate/MeCN=1/0 to 10/1). Compound 6-methyl-2-(6-pyrrolidin-1-ylpyrazin-2-yl)-1,3,6,2-dioxazaborocane-4,8-dione (1.60 g, 5.26 mmol, 63.39% yield) was obtained as a white solid.

$^1$H NMR (400 MHz, CD$_3$CN) 7.96 (s, 1H), 7.89 (s, 1H), 4.11 (d, J=16.8 Hz, 2H), 4.03 (d, J=16.8 Hz, 2H), 3.48-3.42 (m, 4H), 2.70 (s, 3H), 2.04-1.99 (m, 4H)

Step 4. Synthesis of potassium; difluoro-(6-pyrrolidin-1-ylpyrazin-2-yl)borane; fluoride

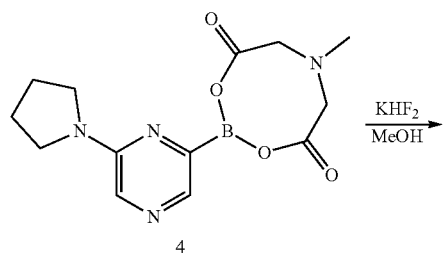

To a solution of 6-methyl-2-(6-pyrrolidin-1-ylpyrazin-2-yl)-1,3,6,2-dioxazaborocane-4,8-dione (1.00 g, 3.29 mmol, 1.00 eq) in MeOH (10.00 mL) was added KHF$_2$ (4.5 M in water, 1.32 mL, 1.80 eq). The mixture was stirred at 30° C. for 1 hour. TLC indicated ~10% of reactant 4 was remained, and one major new spot was detected. The mixture was filtered and the filter cake was dried to give the product. The product was not purified. Compound potassium; difluoro-(6-pyrrolidin-1-ylpyrazin-2-yl)borane; fluoride (300.00 mg, 1.18 mmol, 35.75% yield) was obtained as a white solid LCMS (ESI) m/z 198.1 [MKF+H]$^+$ $^1$H NMR (400 MHz, ACETONITRILE-d3) 8.38 (s, 1H), 7.94 (s, 1H), 3.61 (br t, J=6.4 Hz, 4H), 2.12-2.06 (m, 4H)

$^{19}$F NMR (377 MHz, ACETONITRILE-d3)-145.13 (br dd, J=41.2, 82.4 Hz, 3F)

$^{11}$B NMR (128 MHz, ACETONITRILE-d3) 1.48-0.17 (m, 1B)

Example 8

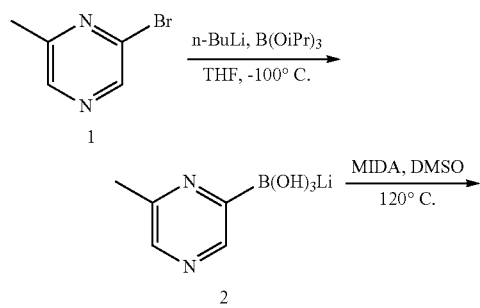

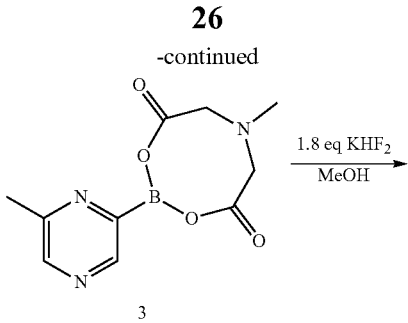

Step 1. Synthesis of hydroxylithium;(6-methylpyrazin-2-yl)boronic acid ES5002-267-P1

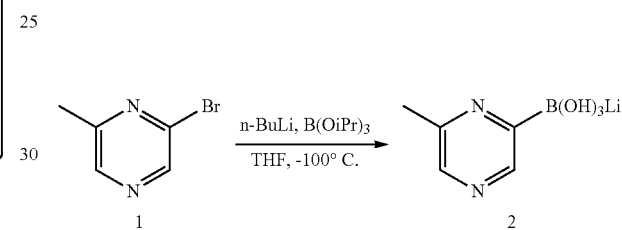

To a solution of 2-bromo-6-methyl-pyrazine (3.10 g, 17.92 mmol, 1.00 eq) and TRIISOPROPYL BORATE (4.04 g, 21.50 mmol, 4.93 mL, 1.20 eq) in THF (30.00 mL) was added n-BuLi (2.5 M in n-hexane, 7.88 mL, 1.10 eq) dropwise at 100° C. The mixture was stirred at 100° C. for 1 hour. TLC indicated reactant 1 was consumed completely and many new spots formed. The crude product hydroxylithium;(6-methylpyrazin-2-yl)boronic acid (2.90 g, crude) in THF (30 mL) was used into the next step without further purification. 0.5 mL of the mixture was quenched by MeOH (3 mL) and confirmed by HNMR.

$^1$H NMR (400 MHz, D$_2$O) 8.26 (s, 1H), 7.98 (s, 1H), 2.30 (s, 3H)

$^1$H NMR (400 MHz, D$_2$O) δ=8.26 (s, 1H), 7.98 (s, 1H), 2.30 (s, 3H).

Step 2. Synthesis of 6-methyl-2-(6-methylpyrazin-2-yl)-1,3,6,2-dioxazaborocane-4,8-dione

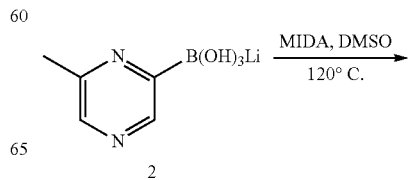

-continued

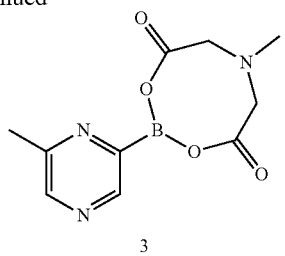

3

To a solution of 2-[carboxymethyl(methyl)amino]acetic acid (3.95 g, 26.87 mmol, 1.50 eq) in DMSO (35.00 mL) was added a solution of hydroxylithium;(6-methylpyrazin-2-yl)boronic acid ester (2.90 g, 17.91 mmol, 1.00 eq) in THF (30 mL) dropwise at 120° C. The mixture was stirred at 120° C. for 1 hr. TLC indicated reactant 2 was consumed completely. The mixture was concentrated under reduced pressure. The residue was purified by column chromatography (SiO$_2$, Petroleum ether/Ethyl acetate/Acetonitrile=2/1/0 to 0/10/1). Compound 6-methyl-2-(6-methylpyrazin-2-yl)-1,3,6,2-dioxazaborocane-4,8-dione (1.10 g, 4.42 mmol, 24.66% yield) was obtained as a white solid.

$^1$H NMR (400 MHz, ACETONITRILE-d3) 8.58 (s, 1H), 8.44 (s, 1H), 4.19-4.10 (m, 2H), 4.06-3.97 (m, 2H), 2.62 (s, 3H), 2.54 (s, 3H)

Step 3. Synthesis of potassium; difluoro-(6-methylpyrazin-2-yl)borane; Fluoride ES5002-277-P1

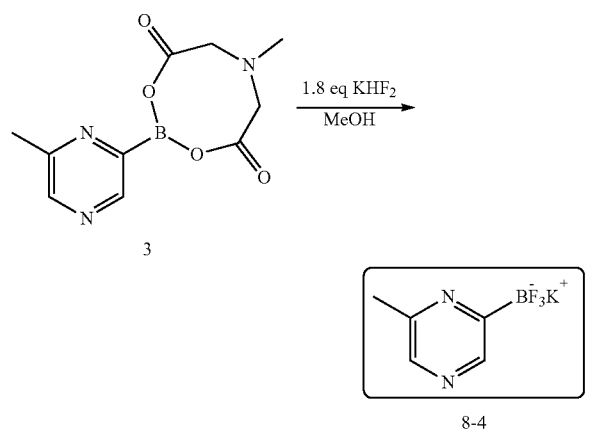

To a solution of 6-methyl-2-(6-methylpyrazin-2-yl)-1,3,6,2-dioxazaborocane-4,8-dione (400.00 mg, 1.61 mmol, 1.00 eq) in MeOH (4.00 mL) was added KHF$_2$ (4.5 M in water, 644.00 uL, 1.80 eq). The mixture was stirred at 30° C. for 12 hour. TLC indicated ~10% of reactant 3 was remained, and one major new spot with larger polarity was detected. The mixture was filtered and the filter cake was dried to give the product. Compound potassium; difluoro-(6-methylpyrazin-2-yl)borane; fluoride (120.00 mg, 582.74 umol, 36.19% yield, 97.128% purity) was obtained as a white solid.

LCMS (ESI) m/z 143.1 [MKF+H]$^+$ $^1$H NMR (400 MHz, ACETONITRILE-d3) 9.11 (s, 1H), 8.95 (s, 1H), 2.71 (s, 3H)

$^{19}$F NMR (377 MHz, ACETONITRILE-d3)-145.22 (br dd, J=40.1, 79.0 Hz, 3F)

$^{11}$B NMR (128 MHz, ACETONITRILE-d3) 1.60-0.44 (m, 1B)

Example 9

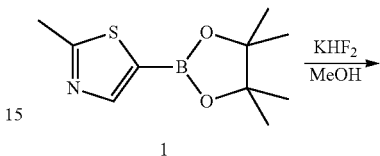

1

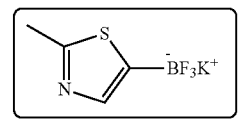

9-2

Step 1. Synthesis of [trifluoro-(2-methylthiazol-5-yl)-λ$^5$-boranyl]potassium(1+)

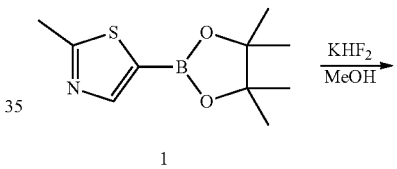

1

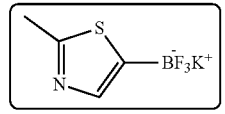

9-2

To a solution of 2-methyl-5-(4,4,5,5-tetramethyl-1,3,2-dioxaborolan-2-yl)thiazole (0.5 g, 2.22 mmol, 1 eq) in MeOH (5 mL) was added KHF$_2$ (4.5 M in water, 888.43 uL, 1.8 eq). The mixture was stirred at 30° C. for 12 hrs. TLC indicated reactant 1 was consumed completely. The mixture was concentrated under reduced pressure. The residue was washed with MeCN (5 mL×3) and filtered. The filtrate was concentrated under reduced pressure. The residue was washed with EtOAc (10 mL×3) and filtered. The filter cake was dried and recrystallized from MeCN (5 mL) to give the product. Compound [trifluoro-(2-methylthiazol-5-yl)-λ$^5$-boranyl]potassium(1+) (150 mg, 731.53 umol, 32.94% yield, 100% purity) was obtained as a white solid.

LCMS (ESI) m/z 148.0 [MKF+H]$^+$ $^1$H NMR (400 MHz, ACETONITRILE-d3) 7.36 (s, 1H), 3.00 (s, 3H)

$^{19}$F NMR (377 MHz, ACETONITRILE-d3)-135.93 (br dd, J=44.6, 90.4 Hz, 3F)

$^{11}$B NMR (128 MHz, ACETONITRILE-d3) 2.19 (br d, J=45.2 Hz, 1B)

Example 10

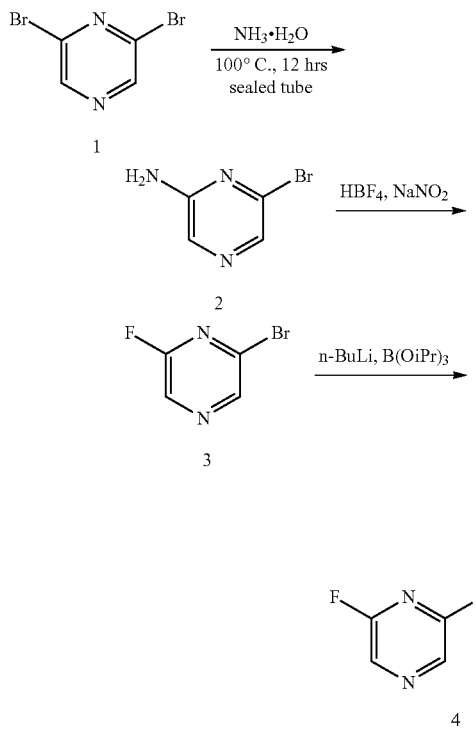

Step 1. Synthesis of 6-bromopyrazin-2-amine

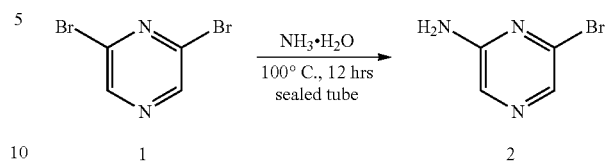

The mixture of 2,6-dibromopyrazine (20 g, 84.08 mmol, 1 eq) and $NH_3 \cdot H_2O$ (36.83 g, 294.27 mmol, 40.47 mL, 3.5 eq) was stirred at 100° C. for 12 hr in a sealed tube. TLC indicated Reactant 1 was consumed completely and one new spot formed. The mixture was filtered; the filter cake was washed with petroleum ether (200 mL×2) and dried under vacuum to give the product. The petroleum ether layer was dried over $Na_2SO_4$, filtered and concentrated under reduced pressure to recover the Reactant 1. The product was used directly in the next step without further purification. Compound 6-bromopyrazin-2-amine (50 g, 287.36 mmol, 68.36% yield) was obtained as a pale solid.

$^1H$ NMR (400 MHz, $CDCl_3$) 7.99 (s, 1H), 7.88 (s, 1H), 4.78 (br s, 2H)

Step 2. Synthesis of 2-bromo-6-fluoropyrazine

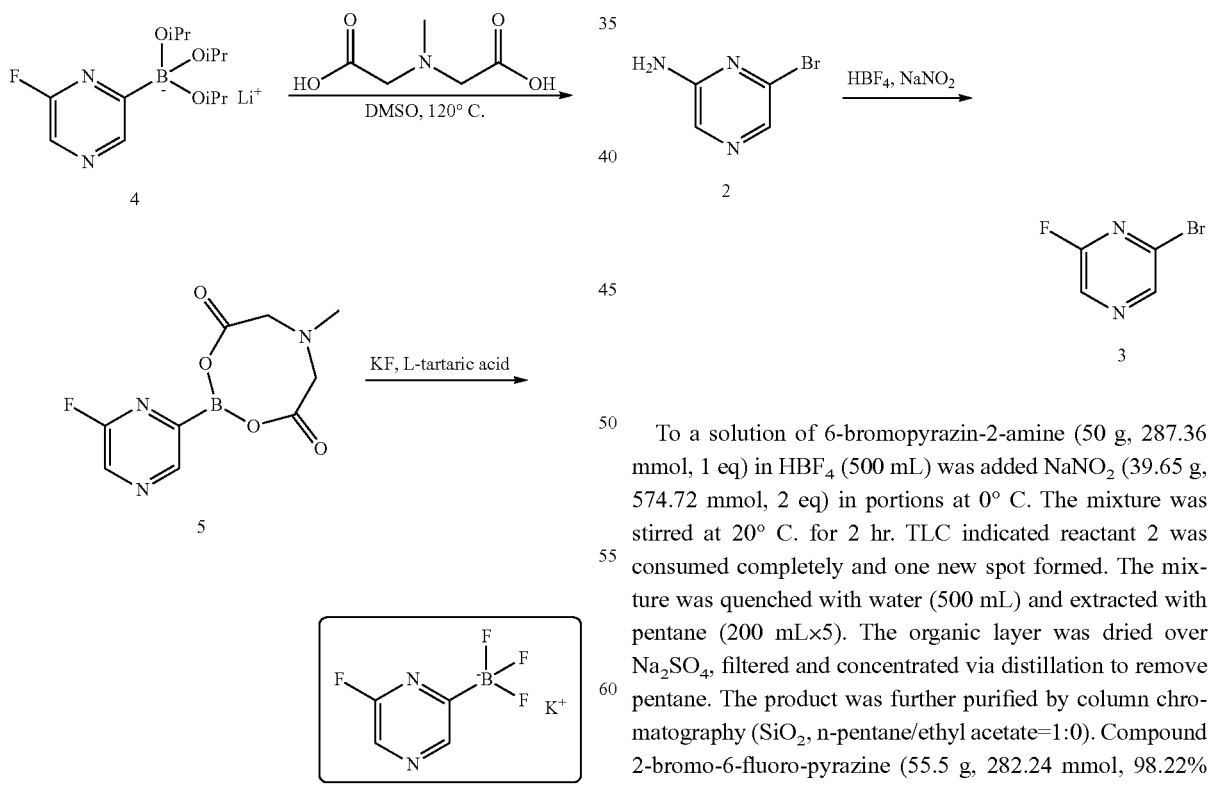

To a solution of 6-bromopyrazin-2-amine (50 g, 287.36 mmol, 1 eq) in $HBF_4$ (500 mL) was added $NaNO_2$ (39.65 g, 574.72 mmol, 2 eq) in portions at 0° C. The mixture was stirred at 20° C. for 2 hr. TLC indicated reactant 2 was consumed completely and one new spot formed. The mixture was quenched with water (500 mL) and extracted with pentane (200 mL×5). The organic layer was dried over $Na_2SO_4$, filtered and concentrated via distillation to remove pentane. The product was further purified by column chromatography ($SiO_2$, n-pentane/ethyl acetate=1:0). Compound 2-bromo-6-fluoro-pyrazine (55.5 g, 282.24 mmol, 98.22% yield, 90% purity) was obtained as brown oil.

$^1H$ NMR (400 MHz, $CDCl_3$) 8.65 (d, J=4.0 Hz, 1H), 8.40 (d, J=8.0 Hz, 1H)

Step 3. Synthesis of [(6-fluoropyrazin-2-yl)-triiso-propoxy-boranyl]lithium(1+)

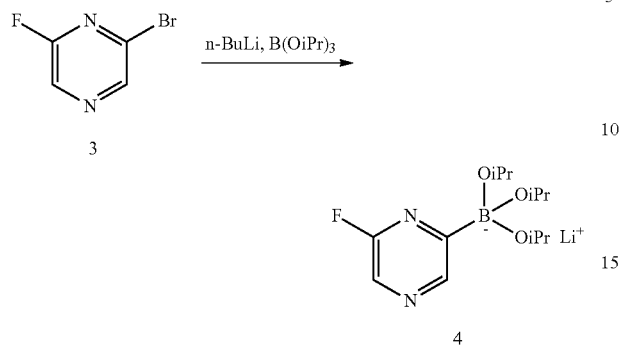

To a solution of 2-bromo-6-fluoro-pyrazine (37.7 g, 213.03 mmol, 1 eq) and TRIISOPROPYL BORATE (44.97 g, 234.33 mmol, 54.97 mL, 98% purity, 1.1 eq) in THF (400 mL) was added n-BuLi (2.5 M in n-hexane, 89.47 mL, 1.05 eq) drop-wise at 90° C. under $N_2$. During which the temperature was maintained below 85° C. The reaction mixture was stirred at 85° C. for 20 min under $N_2$ atmosphere. TLC (petroleum ether/Ethyl acetate=5:1) showed the starting material was consumed completely. The mixture was used directly in the next step. The crude product [(6-fluoropyrazin-2-yl)-triisopropoxy-boranyl]lithium(1+) (62.22 g, crude) in THF (400 mL) as a red-black solvent was used into the next step without further purification.

Step 4. Synthesis of 2-(6-fluoropyrazin-2-yl)-6-methyl-1,3,6,2-dioxazaborocane-4,8-dione

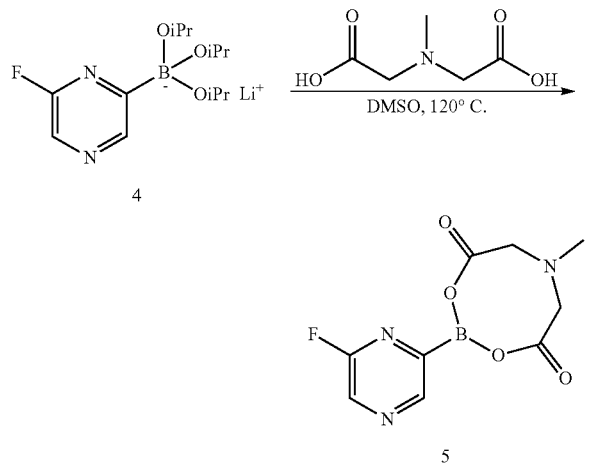

To a solution of 2-[carboxymethyl(methyl)amino]acetic acid (93.99 g, 638.86 mmol, 3 eq) in DMSO (300 mL) was added a solution of [(6-fluoropyrazin-2-yl)-triisopropoxy-boranyl]lithium(1+) (62.2 g, 212.95 mmol, 1 eq) in THF (400 mL) at while keeping the temperature not lower than 80° C. After the addition, the mixture was stirred at 120° C. for 20 min. TLC indicated Reactant 4 was consumed completely and many new spots formed. The mixture was concentrated under reduced pressure. The residue was purified by column chromatography (SiO$_2$, Petroleum ether/Ethyl acetate/acetonitrile=1/1/0 to 0/50/1) to give the crude. The crude was washed with EtOAc (80 mL) and filtered; the filter cake was dried to give the product. Compound 2-(6-fluoropyrazin-2-yl)-6-methyl-1,3,6,2-dioxazaborocane-4,8-dione (16.5 g, 65.22 mmol, 30.63% yield) was obtained as a pink solid.

$^1$H NMR (400 MHz, ACETONITRILE-d3) 8.76 (d, J=4.8 Hz, 1H), 8.48 (d, J=8.0 Hz, 1H), 4.17 (d, J=17.2 Hz, 2H), 4.01 (d, J=16.8 Hz, 2H), 2.67 (s, 3H)

Step 5. Synthesis of potassium trifluoro(6-fluoropyrazin-2-yl)borate

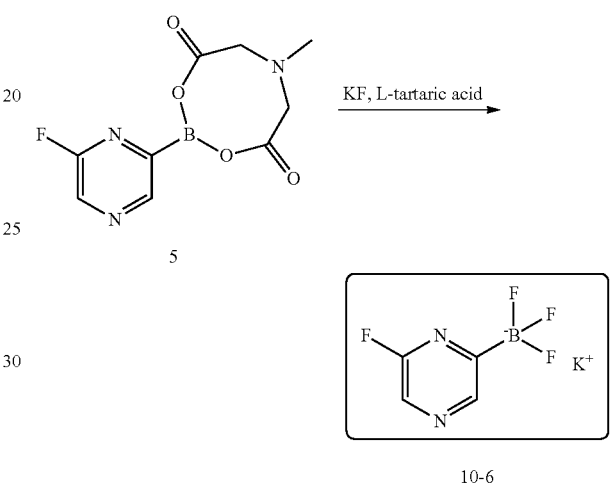

To a solution of 2-(6-fluoropyrazin-2-yl)-6-methyl-1,3,6,2-dioxazaborocane-4,8-dione (34.5 g, 136.37 mmol, 1 eq) in MeCN (545 mL) was added KF (10 M, 54.55 mL, 4 eq) and a solution of TARTARIC ACID (41.96 g, 279.55 mmol, 2.05 eq) in THF (204 mL). The mixture was stirred at 25° C. for 12 hr. TLC indicated Reactant 5 was consumed completely and one new spot formed. The mixture was filtered and the filtrate was concentrated under reduced pressure. The residue was recrystallized from MeCN (1.2 L). Compound potassium trifluoro(6-fluoropyrazin-2-yl)borate (6 g, 29.42 mmol, 21.57% yield) was obtained as a pale gray solid.

LCMS (ESI) m/z 164.7 [MK]$^-$ $^1$HNMR (400 MHz, ACETONITRILE-d3) 8.54 (d, J=6.0 Hz, 1H), 8.17 (d, J=8.3 Hz, 1H)

$^{19}$FNMR (400 MHz, ACETONITRILE-d3)-84.37 (br s, 1F), 144.77 (br dd, J=45.8, 93.8 Hz, 3F)

$^{11}$BNMR (400 MHz, ACETONITRILE-d3) 2.42-0.68 (m, 1B)

Example 11

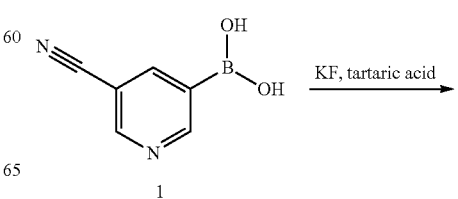

Example 12

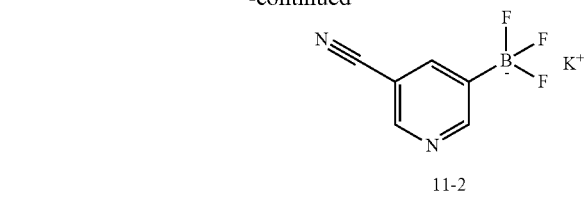

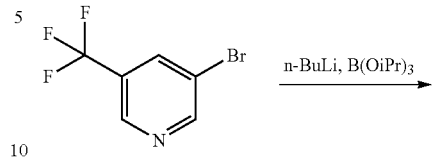

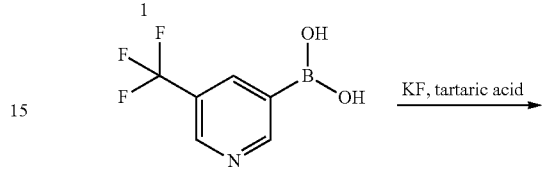

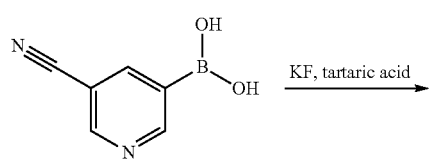

Step 1. Synthesis of potassium (5-cyanopyridin-3-yl)trifluoroborate

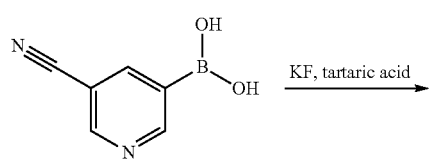

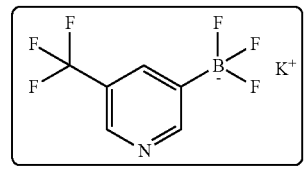

Step 1. Synthesis of [5-(trifluoromethyl)-3-pyridyl]boronic acid

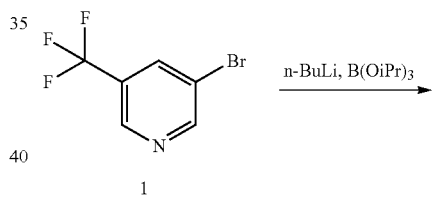

To a solution of (5-cyano-3-pyridyl)boronic acid (50 g, 338.00 mmol, 1 eq) in MeCN (1352 mL) was added a solution of KF (78.55 g, 1.35 mol, 31.67 mL, 4 eq) in H₂O (135.2 mL) and a solution of TARTARIC acid (104.00 g, 692.91 mmol, 2.05 eq) in THF (507 mL). The mixture was stirred at 25° C. for 12 hr. TLC indicated Reactant 1 was consumed completely and one new spot formed. The mixture was filtered and the filtrate was concentrated under reduced pressure.

Compound [(5-cyano-3-pyridyl)-trifluoro-boranyl]potassium(1+) (65 g, 309.52 mmol, 91.57% yield) was obtained as a white solid.

Recrystallization condition: 11-2

The starting material was dissolved with MeOH/CH₃CN (1/2, 1 g/30 mL). The suspension was heated to 80° C. until the product was dissolved mainly. The suspension solution was filtered immediately before it was cooled to room temperature. And the filtrate was cooled to 20° C., then the crystal was formed. The mixture was filtered and the filter cake was washed with CH₃CN/MeOH (2/1, 100 mL) and the filter cake was dried under reduced pressure to give a white crystal.

LCMS (ESI) m/z 152.0 [MKF+H]⁺

$^1$HNMR (400 MHz, ACETONITRILE-d₃) 8.76 (br s, 1H), 8.67 (br s, 1H), 8.10 (br s, 1H)

$^{19}$FNMR (400 MHz, ACETONITRILE-d₃) -142.15--142.56 (q, 3F)

$^{11}$BNMR (400 MHz, ACETONITRILE-d₃) 3.0-2.05 (q, 1B)

$^{13}$CNMR (400 MHz, ACETONITRILE-d₃) 156.04 (s, 1C), 149.37 (s, 1C), 141.64 (s, 1C), 118.15 (s, 1C), 99.68 (s, 1C)

To a solution of 3-bromo-5-(trifluoromethyl)pyridine (100 g, 442.49 mmol, 1 eq) and TRIISOPROPYL BORATE (99.86 g, 530.99 mmol, 122.08 mL, 1.2 eq) in THF (1000 mL) was added n-BuLi (2.5 M in n-hexane, 194.70 mL, 1.1 eq) dropwise at 78° C. under N₂ atmosphere. The mixture was stirred at 78° C. for 1 hr under N₂ atmosphere. TLC indicated reactant 1 was consumed completely. The mixture was quenched with water (100 mL) at 10° C., and acidified by HCl (1N) to pH=5. The mixture was extracted with EtOAc (200 mL×3). The organic layer was dried over Na₂SO₄, filtered and concentrated under reduced pressure. The residue was washed with EtOAc (100 mL) and filtered. The filter cake was dried to give the product. Compound [5-(trifluoromethyl)-3-pyridyl]boronic acid (50.8 g, 266.09 mmol, 60.13% yield) was obtained as a white solid.

$^1$H NMR (400 MHz, DMSO) 9.07 (s, 1H), 8.94 (s, 1H), 8.39 (s, 1H)

Step 2. Synthesis of potassium (5-cyanopyridin-3-yl)trifluoroborate

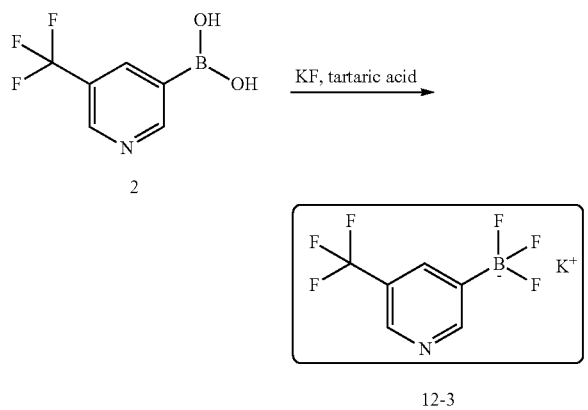

To a solution of [5-(trifluoromethyl)-3-pyridyl]boronic acid (50.8 g, 266.09 mmol, 1 eq) in MeCN (1064 mL) was added a solution of KF (61.83 g, 1.06 mol, 24.93 mL, 4 eq) in $H_2O$ (106 mL) and a solution of TARTARIC ACID (81.87 g, 545.48 mmol, 2.05 eq) in THF (400 mL). The mixture was stirred at 30° C. for 12 hr. TLC indicated Reactant 2 was consumed completely and one new spot formed. The mixture was filtered and the filtrate was concentrated under reduced pressure. The residue was washed with MeOH (100 mL) and filtered. The filter cake was dried to give the product. Compound [trifluoro-[5-(trifluoromethyl)-3-pyridyl]-boranyl]potassium(1+) (70 g, crude) was obtained as a white solid.

$^1$H NMR (400 MHz, ACETONITRILE-d3) 8.82 (s, 1H), 8.67 (s, 1H), 8.01 (br s, 1H)

Recrystallization Condition:

The mixture was diluted with $CH_3OH$ (1 g/20 mL) and warmed to 80° C. and stirred for 1 hr. Then the solution was filtered in case of heating and the filter cake was washed with $CH_3OH$ (100 mL) and the filtrate was cooled to 25° C., and the crystalline was formed. Then the suspension was filtered and the filter cake was dried under reduced pressure to give a white crystals.

LCMS (ESI) m/z 214.0 [MK]$^-$ $^1$H NMR (400 MHz, ACETONITRILE-d3) 8.80 (s, 1H), 8.65 (s, 1H), 7.98 (br s, 1H)

$^{19}$F NMR (400 MHz, ACETONITRILE-d3)-57.58 (s, 3H), 137.5-138.5 (m, 3F)

$^{11}$B NMR (400 MHz, ACETONITRILE-d3) 3.32-2.15 (m, 1B)

$^{13}$C NMR (101 MHz, ACETONITRILE-d3) 156.55 (br s, 1C), 143.86 (br s, 1C), 135.68 (br s, 1C), 126.4-123.7 (m, 1C), 125.10 (m, 1C)

Example 13

Scheme

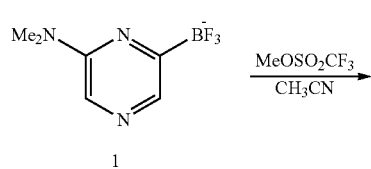

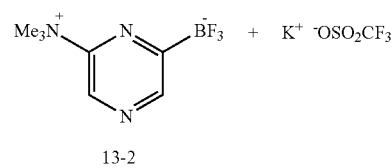

Compound 1 (prepared in Example 5-2) is dissolved in anhydrous acetonitrile and cooled in an ice bath under nitrogen. A dichloromethane solution of methyl trifluoromethanesulfonate (1.1 equivalent) is added dropwise and the reaction mixture is slowly warmed to room temperature. The reaction is quenched by addition of a small amount of water. The solvent is removed under reduced pressure and the precipitate formed is collected by filtration to give product 13-2.

Example 14

Scheme

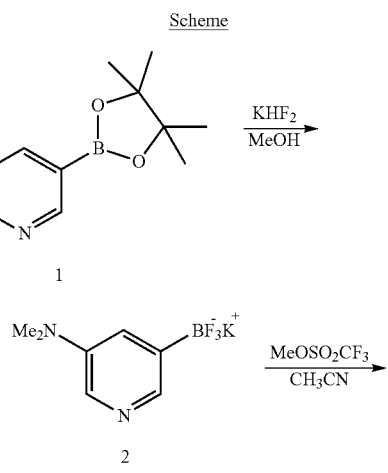

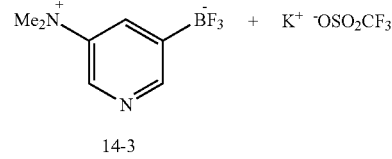

Step 1

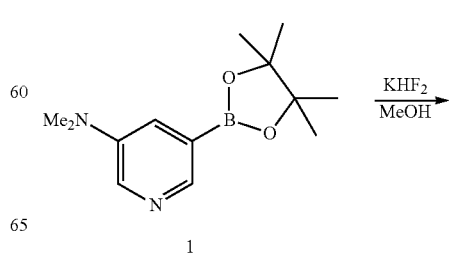

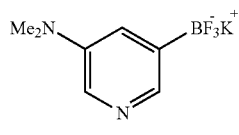

Compound 1 (N,N-dimethyl-5-(4,4,5,5)-tetramethyl-1,3,2-dioxaborolan-2-yl)-3-pyridinamine is commercially available. To a solution of compound 1 in MeOH is added KHF$_2$ (3 equivalent) at room temperature. The solution is stirred at room temperature for 3 hours. The mixture is concentrated under reduced pressure and the residue is washed with EtOAc and the precipitate is collected by filtration to give compound 2.

Step 2

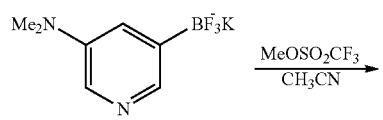

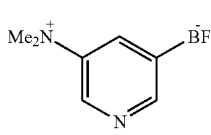

Compound 2 is dissolved in anhydrous acetonitrile and cooled in an ice bath under nitrogen. A dichloromethane solution of methyl trifluoromethanesulfonate (1.1 equivalent) is added dropwise and the reaction mixture is slowly warmed to room temperature. The reaction is quenched by addition of a small amount of water. The solvent is removed under reduced pressure and the precipitate formed is collected by filtration to give product 14-3.

Example 15

Scheme

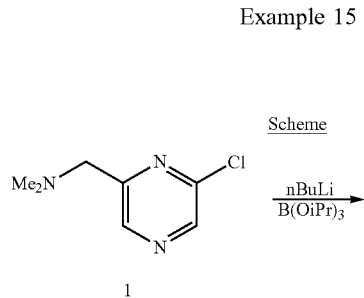

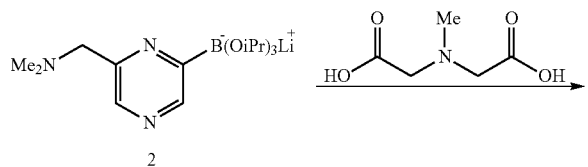

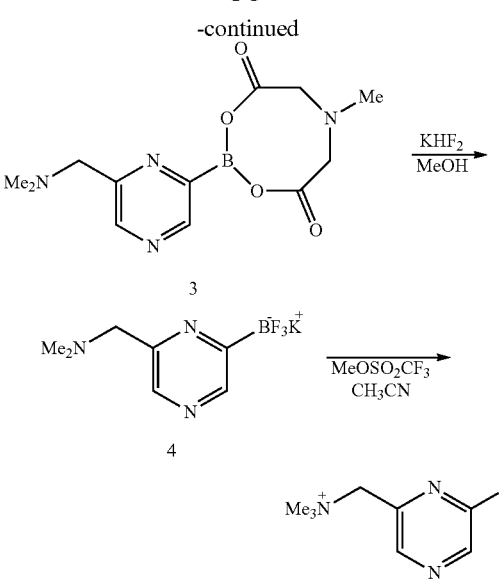

Compound 1, 6-chloro-N,N-dimethyl-2-pyrazinemethanamine is commercially available. To a solution of compound 1 and triisopropyl borate in THF is added n-BuLi/hexane solution (1.2 equivalents) dropwise at 100° C. The crude product 2 is used directly in the next step.

Step 2

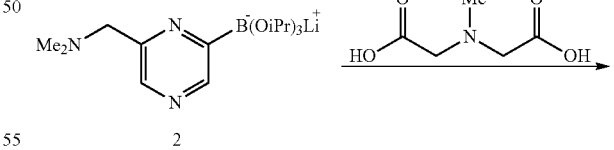

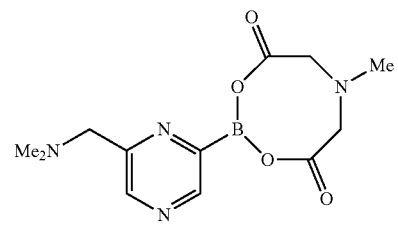

To a solution of 2-[carboxymethyl(methyl)amino]acetic acid (1.5 equivalents) in DMSO is added a solution of compound 2 in THF dropwise at 120° C. The mixture is stirred at 120° C. for 1 hour and the mixture is concentrated under reduced pressure and the residue is purified by column chromatography to give compound 3.

Step 3

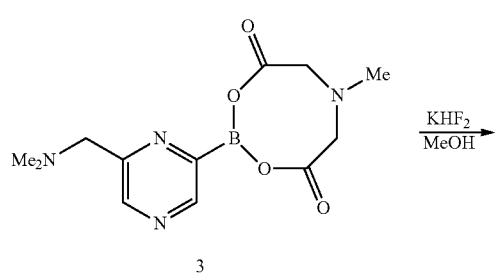

To a solution of compound 3 in MeOH is added KHF$_2$ (1.8 equivalent) in water. The mixture is stirred at 30° C. for 12 hours. The precipitate is collected by filtration and dried to give compound 4.

Step 4

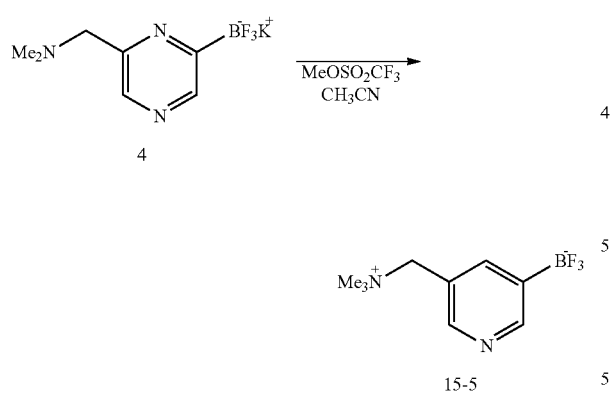

Compound 4 is dissolved in anhydrous acetonitrile and cooled in an ice bath under nitrogen. A dichloromethane solution of methyl trifluoromethanesulfonate (1.1 equivalent) is added dropwise and the reaction mixture is slowly warmed to room temperature. The reaction is quenched by addition of a small amount of water. The solvent is removed under reduced pressure and the precipitate formed is collected by filtration to give product 15-5.

Example 16

Scheme

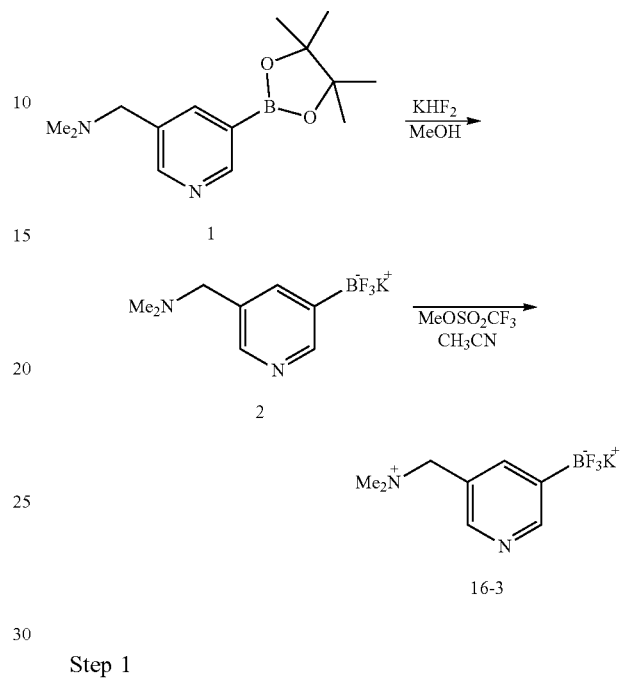

Step 1

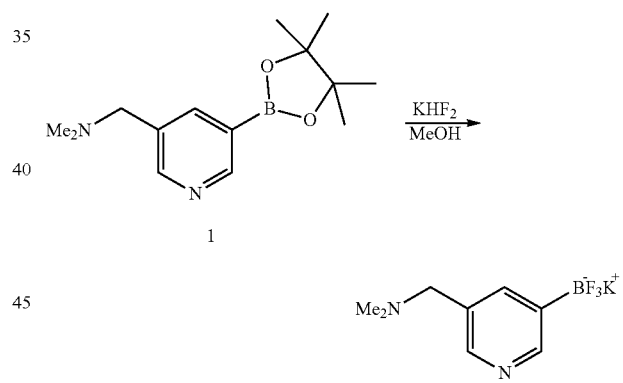

Compound 1 is commercially available. To a solution of compound 1 in MeOH is added KHF$_2$ (1.8 equivalents) in water. The mixture is stirred at 30° C. for 12 hours. The precipitate is collected by filtration and dried to give compound 2.

Step 2

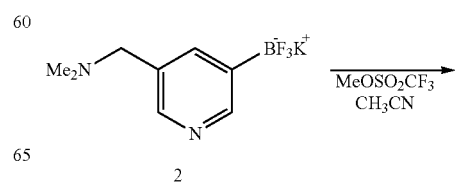

-continued

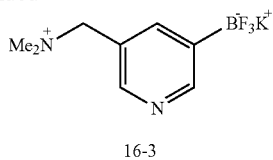

16-3

Compound 2 is dissolved in anhydrous acetonitrile and cooled in an ice bath under nitrogen. A dichloromethane solution of methyl trifluoromethanesulfonate (1.1 equivalent) is added dropwise and the reaction mixture is slowly warmed to room temperature. The reaction is quenched by addition of a small amount of water. The solvent is removed under reduced pressure and the precipitate formed is collected by filtration to give product 16-3.

Example 16

Biological Experiments

MIC (Minimum Inhibitory Concentration) determination of anti-tuberculosis drugs

The antituberculosis activity of each compound against M tb H37Rv was measured by the green fluorescent protein reporter assay (L. A. Collins, M. N. Torrero, S. G. Franzblau, *Antimicrob. Agents Chemother.* 1998, 42, 344-347). Briefly, the compound was initially dissolved in dimethylsulfoxide (DMSO), and two fold dilutions were made in DMSO. The same amount of each dilution of compound solution was added to 7H9 broth in microplates. The initial inoculum of $2\times10^5$ CFU/ml of Mtb H37Rv-GFP that was grown in Middlebrook 7H9 media was exposed to the compound for 10 days. The fluorescence was measured in a Fluostar Optima microplate fluorometer (BMG Labtech, Germany), and the MIC was defined as the lowest concentration of compounds that inhibited fluorescence by 90% comparing to the fluorescence of bacteria only wells. CFU=colony forming units.

Table 1 below shows activity of representative compounds of the invention and reference compound pyrazinamide against Mtb H37Rv MtbH37Rv pncA-knock out strians at pH 6.7 and 5.2. MIC6.7WT means MIC against wild type Mtb at pH 6.7 whereas MIC5.2WT means MIC at pH 5.2 against the wild type Mtb. MIC6.7KO means MIC against a pncA knock-out strain of Mtb at pH6.7 whereas MIC5.2KO means MIC against the same knock out strain at pH5.2. This table indicates that the compounds prepared are active against WT M tb only at low pH such as pH 5.2 like PZA and that they are active against a pncA knock out strain of M tb suggesting they are active against PZA-resistant (due to mutations in pncA) strains of M tb.

| Compound ID | Structure | MIC 6.7 WT (μM) | MIC 5.2 WT (μM) | MIC 6.7 KO (μM) | MIC 5.2 KO (μM) | Vero cell IC50 (μM) |
|---|---|---|---|---|---|---|
| 1-4 | 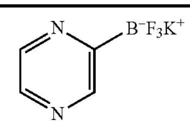 | >200 | 100 | >200 | 100 | >100 |
| 2-5 | 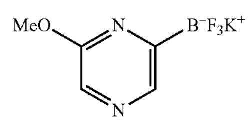 | >200 | 50 | >200 | 25 | >100 |
| 3-5 | 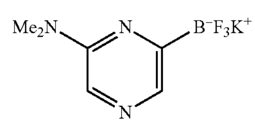 | NA | NA | NA | NA | NA |
| 4-2 | 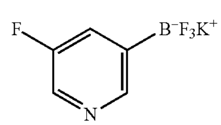 | 200 | 50 | 100 | 25 | >100 |
| 5-2 | 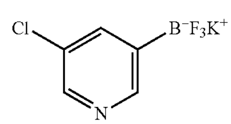 | 100 | 50 | 100 | 50 | >100 |
| 6-2 | 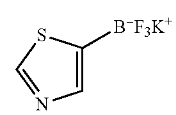 | >200 | 50 | >200 | 50 | >100 |
| 7-5 | 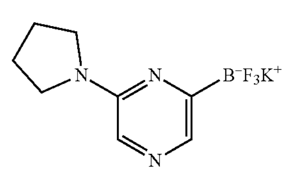 | >200 | 100 | >200 | 50 | >100 |

-continued

| Compound ID | Structure | MIC 6.7 WT (μM) | MIC 5.2 WT (μM) | MIC 6.7 KO (μM) | MIC 5.2 KO (μM) | Vero cell IC50 (μM) |
|---|---|---|---|---|---|---|
| 8-4 | 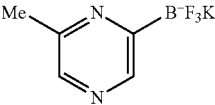 | >200 | 50 | >200 | 25 | >100 |
| 9-2 | 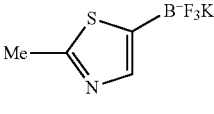 | NA | NA | NA | NA | NA |
| 10-6 | 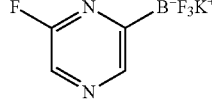 | >200 | 100 | >200 | 100 | >100 |
| 11-2 | 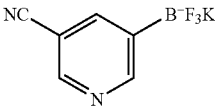 | >200 | 100 | >200 | 100 | >100 |
| 12-3 | 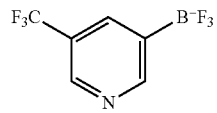 | >200 | 100 | >200 | 100 | >100 |
| Pyrazinamide (PZA) | 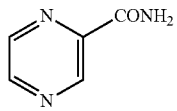 | >400 | 100 | >400 | >400 | >100 |

MIC at pH 5.2

The antituberculous activity of each compound against M tb H37Rv at pH 5.2 was measured by the green fluorescent protein reporter assay. (L. A. Collins, M. N. Torrero, S. G. Franzblau, *Antimicrob. Agents Chemother.* 1998, 42, 344-347).

Briefly, the compound was initially dissolved in dimethylsulfoxide (DMSO), and two fold dilutions were made in DMSO. The same amount of each dilution of compound solution was added to pH-adjusted 7H9 broth in microplates. The initial inoculum of $2\times10^7$ CFU/ml of Mtb H37Rv-GFP that was grown in Middlebrook 7H9 media. The inoculum was harvested and resuspended in pH-adjusted 7H9 broth. The inoculum was exposed to the compound for 10 days. The fluorescence was measured in a Fluostar Optima microplate fluorometer (BMG Labtech, Germany), and the MIC was defined as the lowest concentration of compounds that inhibited fluorescence by 80% comparing to the fluorescence of bacteria only wells.

Mammalian Cell Toxicity Assay

The cytotoxicity of a compound against mammalian Vero cells were measured using CellTiter 96® Non-Radioactive Cell Proliferation Assay (Promega). Briefly, the compound was initially dissolved in dimethylsulfoxide (DMSO), and two fold dilutions were made in DMSO. Vero cells were grown in Dulbecco's modification of Eagle medium (DMEM), supplemented with 10% heat-inactivated fetal bovine for 48 hours. The cells were counted and suspend the cells to a final concentration of $1\times10^5$/ml in DMEM medium. The 50 μl of the cell suspension (5,000 cells) was dispensed into all wells of the 96-well plate that is pre-filled with 50 μl of media, and the 2 ul of each dilution of compound was added. Incubate the plate at 37° C. for 72 hours in a humidified, 5% CO2 atmosphere. The assay is performed by adding a premixed optimized Dye Solution to culture wells of a 96-well plate. After 4 hours the Solubilization/Stop Solution then is added to the culture wells to solubilize the formazan product, and the absorbance at 570 nm is recorded using a 96-well plate reader. The $IC_{50}$ was defined as the lowest concentration of compounds that inhibited absorbance by 50% comparing to the absorbance of Vero cells only wells.

Measurement of Intracellular pH Change in *Mycobacterium*

The change of intracellular pH of *Mycobacterium* was measured using M tb that expressed a pH sensitive green fluorescent protein PH-GFP. (0. H. Vandal, L. M. Pierini, D. Schnappinger, C. F. Nathan, S. Ehrt. *Nat Med.* 2008, 14, 849-854.) Briefly, the compound was initially dissolved in dimethylsulfoxide (DMSO), and two-fold dilutions were made in DMSO. The same amount of each dilution of compound solution was added to 7H9 broth of which pH was adjusted to 5.2 in microplates. The initial inoculum of $2\times10^7$ CFU/ml of Mtb H37Rv-PH-GFP that was grown in Middlebrook 7H9 media. The inoculum was harvested and resuspended in pH-adjusted 7H9 broth. The inoculum was exposed to the compound for 4 days. The fluorescence was measured in a Fluostar Optima microplate fluorometer (BMG Labtech, Germany) each day exciting at absorbances of 395 nm and 475 nm and recording emission at an absorbance of 510 nm. The 395:475 absorbance ratios were calculated and plotted against the time recorded.

Effect on the Internal pH of Mtb

Figure 2:
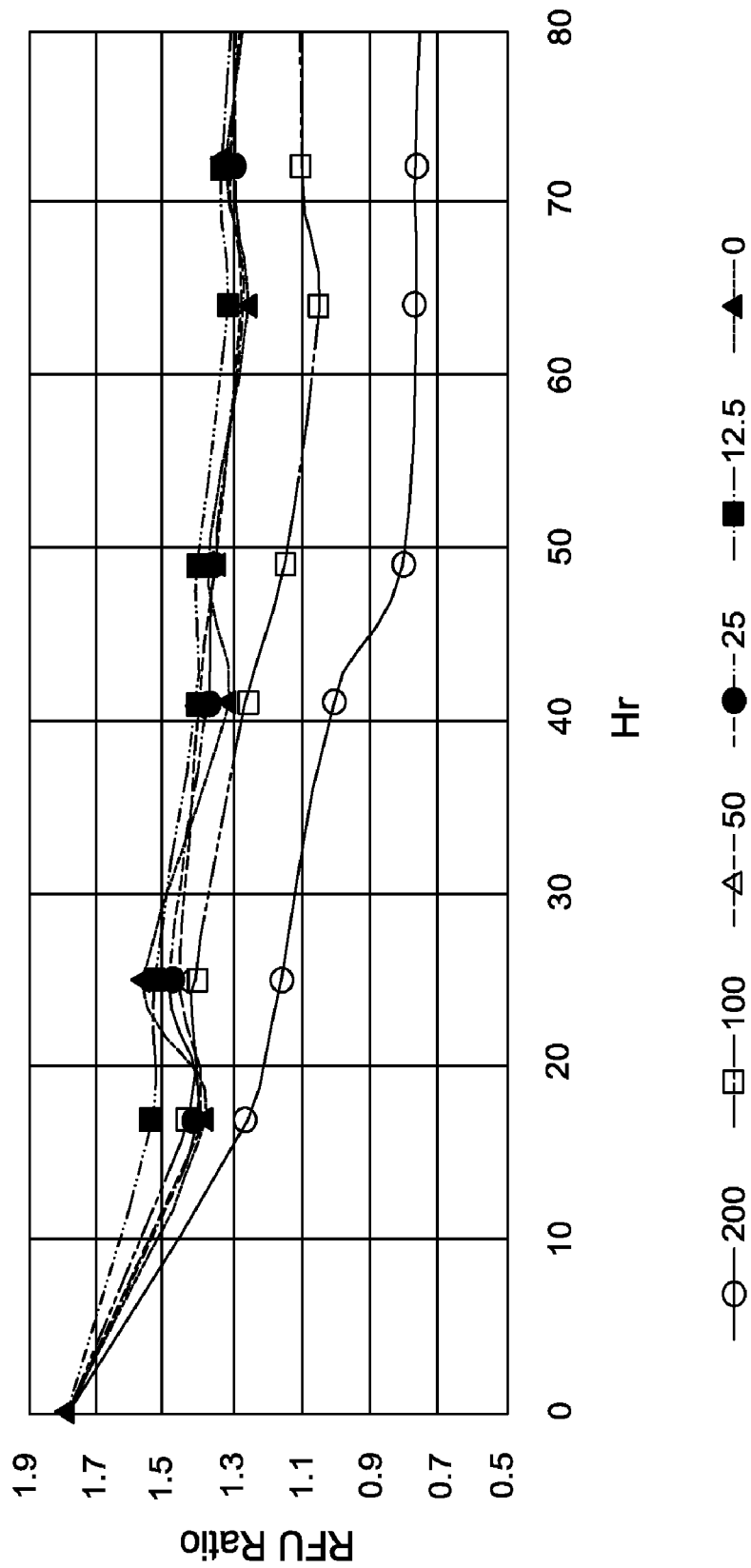
FIG. 2 shows the change in internal pH of Mtb when treated with compound 1-4
Figure 3:
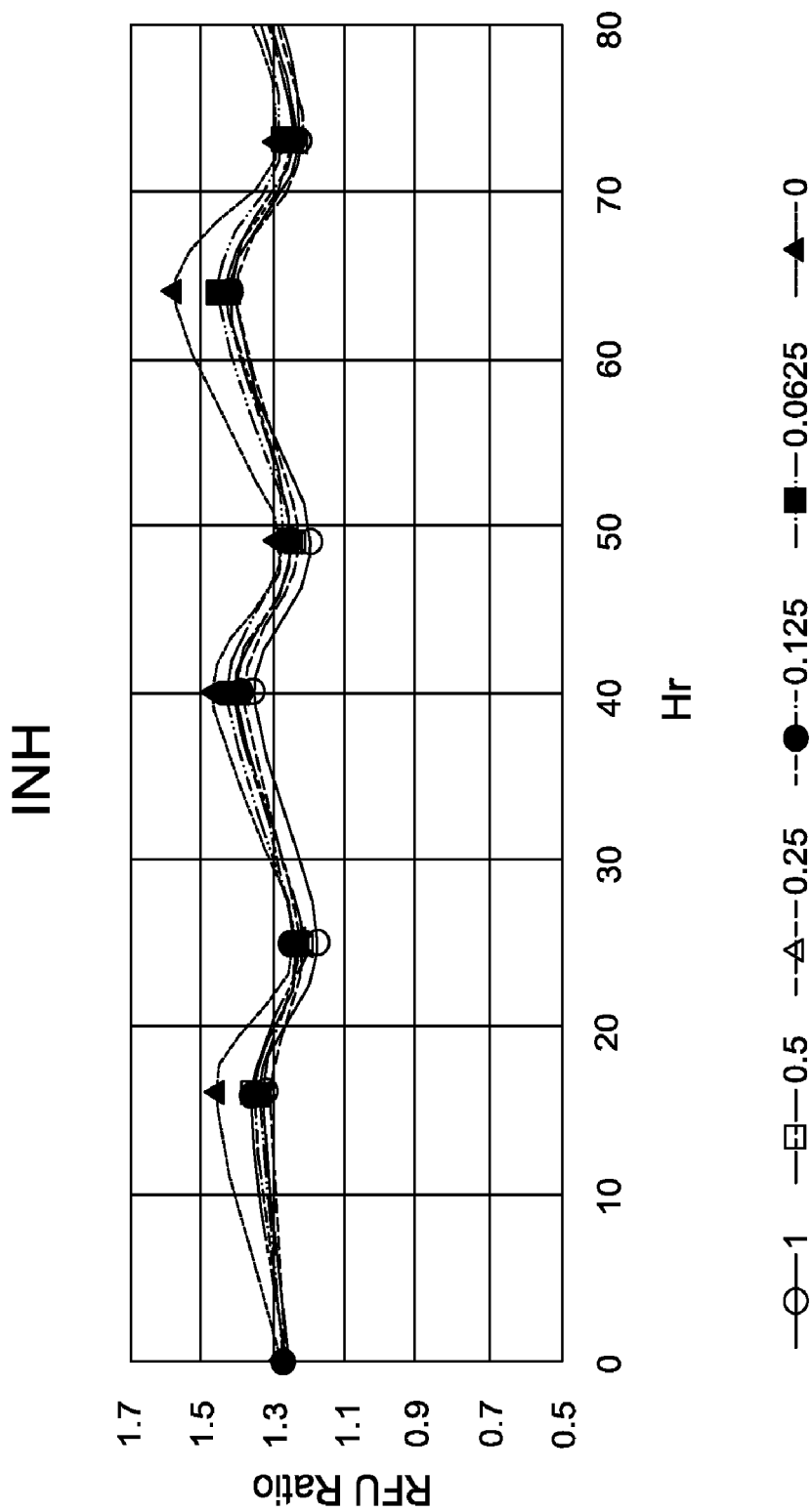
FIG. 3 shows the change in internal pH of Mtb when treated with Isoniazid (INH, negative control compound).

One of the characteristics of PZA is lowering internal pH of Mtb when it is placed in an acidic medium. The internal pH can be measured by modified GFP (Green Fluorescence Protein) and a typical time course and dose response due to PZA is shown in FIG. 1. The change when Mtb is treated with compound 6 is shown in FIG. 2 and it is similar to what is observed with PZA. For comparison, the pH effect of Isoniazid (INH), another TB drug which does not have any effect on internal pH is shown in FIG. 3.

Minimum Inhibitory Concentrations of PZA and Compound 1-4 and Activity Against pncA Knock-Out Strain PZA shows a MIC of 100-200 μM against Mtb at pH 5.2 but it does not exhibit a MIC (MIC>400 μM) at pH 6.7. Compound 6 shows a similar pattern as PZA as indicated in Table 2.

TABLE 2

| Compound (μM) | MIC6.7WT | MIC5.2WT | MIC6.7KO | MIC5.2KO | Vero cell IC50 |
|---|---|---|---|---|---|
| PZA | >400 | 100 | >400 | >400 | >100 |
| Compound 1-4 | >200 | 100 | >200 | 100 | >100 |

PZA requires PncA to be hydrolyzed to POA and therefore it is not active against an Mtb strain whose pncA is knocked out. Compound 1-4 does not require PncA and therefore it is expected to be active against Mtb pncA KO strain. Table 2 indicates that compound 1-4 is active against the pncA KO strain of Mtb.

The invention will be further described, without limitation, by the following numbered paragraphs:

1. A compound of formula (I):

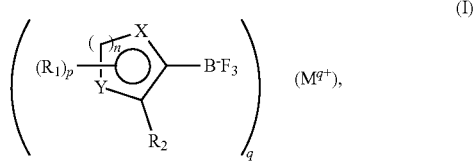

wherein:

X and Y, individually of each other, are C, N, O or S, with the provisos that X and Y are not both C, that X and Y are not both O or S when n is 2, and that X is O or S and Y is N when n is 1;

M is Ca, Cs, K, Li, Mg, Na or tetraalkyl ammonium ion $(R_3)_4N^+$;

$R_1$ is, individually in each occurrence, hydrogen, halogen, alkoxy, halo-alkoxy, lower alkyl, halo-lower alkyl, CN, —$(CH_2)_tCN$, —$NR_3R_4$, cycloalkyl, or heterocycloalkyl;

$R_2$ is hydrogen, halogen, alkoxy, halo-alkoxy, lower alkyl, halo-lower alkyl, CN, —$(CH_2)_tCN$, —$NR_3R_4$, cycloalkyl, or heterocycloalkyl;

$R_3$ and $R_4$, independently of each other, are hydrogen or lower alkyl; or $R_3$ and $R_4$, together with the nitrogen atom to which they are attached, combine to form a 4- to 7-membered ring;

n is 1 or 2;
p is 1 or 2;
q is 1 or 2; and
t is 1, 2, 3 or 4.

2. The compound according to paragraph 1, wherein n is 2 and X and Y are both N.

3. The compound according to paragraph 1, wherein n is 2, X is C and Y is N.

4. The compound according to paragraph 1, wherein n is 2, X is N and Y is C.

5. The compound according to claim 1, wherein n is 2 and M is K, Li or Na.

6. The compound according to claim 1, wherein n is 1 and M is Mg or Ca.

7. The compound according to paragraph 1, wherein $R_1$ is, individually in each occurrence, hydrogen, halogen, alkoxy, halo-alkoxy, lower alkyl or halo-lower alkyl.

8. The compound according to paragraph 1, wherein $R_1$ is, individually in each occurrence, —$CH_2CN$, —$NR_3R_4$ or cyano.

9. The compound according to paragraph 1, wherein $R_1$ is, individually in each occurrence, cycloalkyl or heterocycloalkyl.

10. The compound according to paragraph 1, wherein $R_2$ is hydrogen or halogen.

11. The compound according to paragraph 1, wherein $R_2$ is alkoxy, halo-alkoxy, lower alkyl or halo-lower alkyl.

12. The compound according to paragraph 1, wherein $R_3$ and $R_4$, independently of each other, are hydrogen or lower alkyl.

13. The compound according to paragraph 1, wherein R3 and R4, together with the nitrogen atom to which they are attached, combine to form a 4- to 7-membered ring.

14. The compound according to paragraph 1, wherein n is 1, X is S and Y is N.

15. The compound according to paragraph 1, wherein n is 1, X is N and Y is S.

16. The compound according to paragraph 1, wherein n is 1, X is O and Y is N.

17. The compound according to paragraph 1, wherein n is 1, X is N, and Y is O.

18. The compound according to paragraph 1, wherein p is 1.

19. The compound according to paragraph 1, wherein q is 1.

20. The compound according to paragraph 1, wherein said compound is:

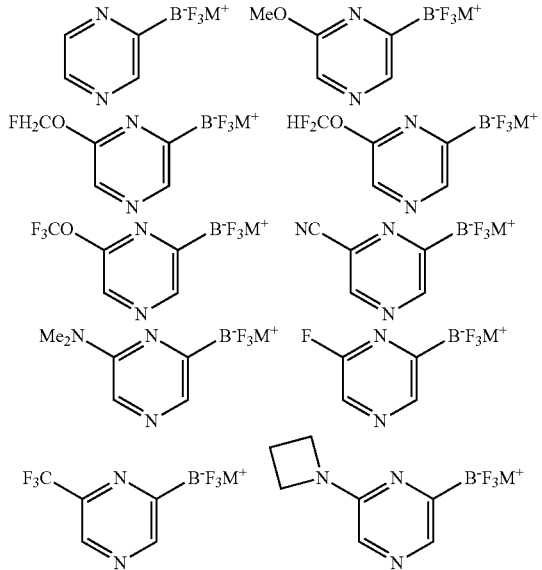

-continued

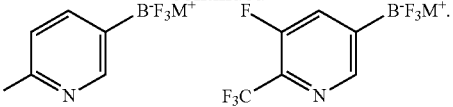

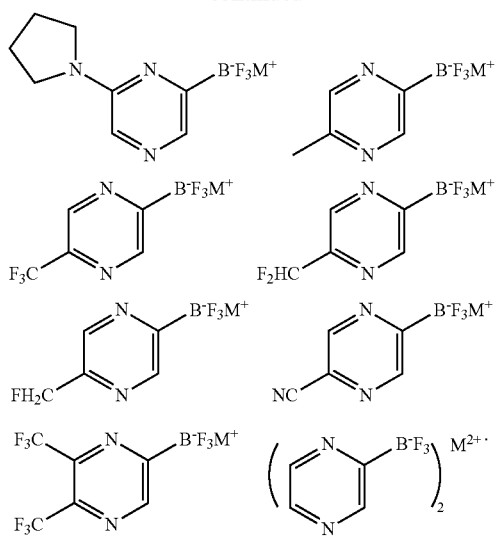

21. The compound according to paragraph 1, wherein said compound is:

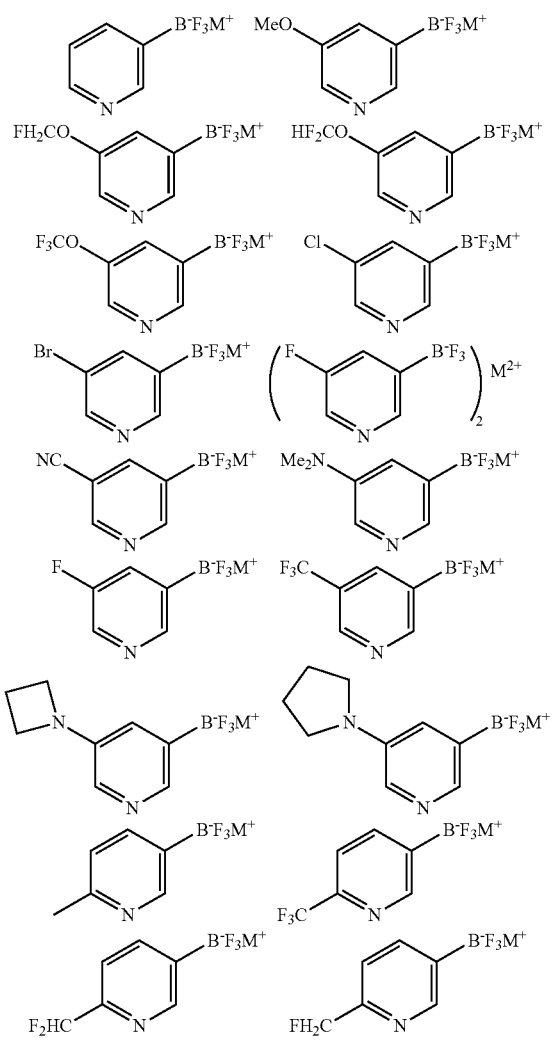

22. The compound according to paragraph 1, wherein said compound is:

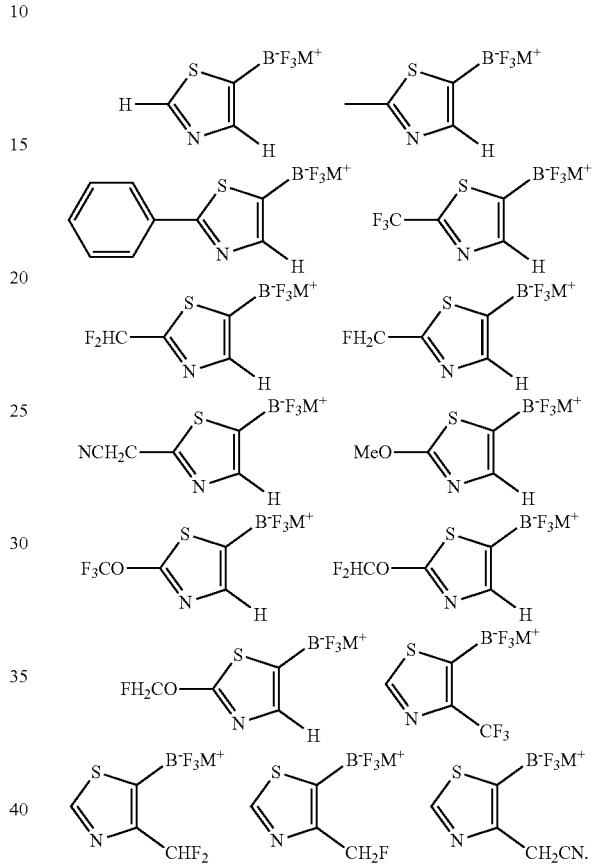

23. The compound according to paragraph 1, wherein said compound is

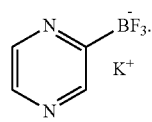

24. A pharmaceutical composition comprising a compound of paragraph 1 and one or more pharmaceutically acceptable carriers and/or additives.

25. The pharmaceutical composition according to paragraph 24, further comprising one or more additional anti-infective agents 26. The pharmaceutical composition according to paragraph 24, wherein said additional anti-infective agent is rifampicin, rifabutin, rifapentene, isoniazid, ethambutol, kanamycin, amikacin, capreomycin, clofazimine, cycloserine, para-aminosalicylic acid, linezolid, sutezolid, bedaquiline, delamanid, pretomanid, moxifloxacin or levofloxacin, or combinations thereof.

27. A method of treating a mycobacterial infection, comprising the step of administering a therapeutically effective amount of a compound of Formula I to a patient in need thereof.

28. The method of paragraph 27, wherein the mycobacterial infection is caused by *Mycobacterium tuberculosis, Mycobacterium avium, Mycobacterium kansasii, Mycobacterium abscessus* or *Mycobacterium chelonae*.

29. The method of paragraph 27, wherein the mycobacterial infection is caused by *Mycobacterium tuberculosis*.

30. A compound of formula (II):

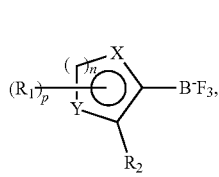

(II)

wherein:

X and Y, individually of each other, are C, N, O or S, with the provisos that X and Y are not both C, that X and Y are not both O or S when n is 2, and that X is O or S and Y is N when n is 1;

$R_1$ is $[(R_3)_3N^+]$— or $[(R_3)_3N^+(CH_2)_s]$—, with the proviso that $R_1$ is not $[(R_3)_3N^+]$— when n is 1;

$R_2$ is hydrogen, halogen, alkoxy, halo-alkoxy, lower alkyl or halo-lower alkyl;

each $R_3$ is, independently, lower alkyl, or two $R_3$'s together with the nitrogen to which they are attached form a 4 to 7-membered ring;

n is 1 or 2;

p is 1 or 2; and s is 1, 2, 3, 4, 5 or 6.

31. The compound according to paragraph 30, wherein $R_1$ is:

32. The compound according to paragraph 30, having formula (IIa):

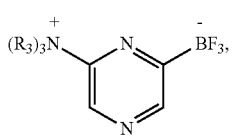

(IIa)

wherein each $R_3$ is, independently, methyl, ethyl, propyl, or isopropyl, or two $R_3$'s together with the nitrogen to which they are attached form a 3 to 5-membered ring.

33. The compound according to paragraph 30, having formula (IIb):

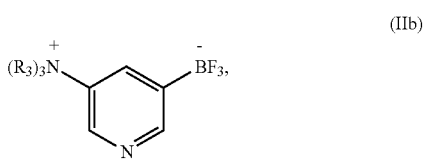

(IIb)

wherein each $R_3$ is, independently, methyl, ethyl, propyl, or isopropyl, or two $R_3$'s together with the nitrogen to which they are attached form a 3 to 5-membered ring.

34. The compound according to paragraph 30, having formula (IIc):

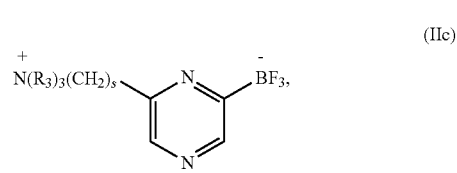

(IIc)

wherein:

each $R_3$ is, independently, methyl, ethyl, propyl, or isopropyl, or two $R_3$'s together with the nitrogen to which they are attached form a 3 to 5-membered ring; and s is 1, 2, 3 or 4.

35. The compound according to paragraph 30, having formula (IId):

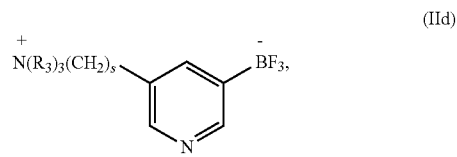

(IId)

wherein:

each $R_3$ is, independently, methyl, ethyl, propyl, or isopropyl, or two $R_3$'s together with the nitrogen to which they are attached form a 3 to 5-membered ring; and s is 1, 2, 3 or 4.

36. The compound according to paragraph 30, having formula (IIe):

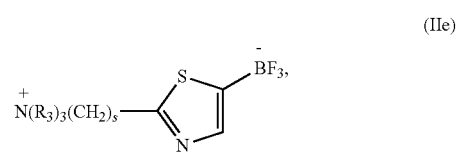

(IIe)

wherein:

each $R_3$ is, independently, methyl, ethyl, propyl, or isopropyl, or two $R_3$'s together with the nitrogen to which they are attached form a 3 to 5-membered ring; and s is 1, 2, 3 or 4.

37. A pharmaceutical composition comprising a compound of paragraph 30 and one or more pharmaceutically acceptable carriers and/or additives.

38. The pharmaceutical composition according to paragraph 37, further comprising one or more additional anti-infective agents 39. The pharmaceutical composition according to paragraph 36, wherein said additional anti-infective agent is rifampicin, rifabutin, rifapentene, isoniazid, ethambutol, kanamycin, amikacin, capreomycin, clofazimine, cycloserine, para-aminosalicylic acid, linezolid, sutezolid, bedaquiline, delamanid, pretomanid, moxifloxacin or levofloxacin, or combinations thereof.

40. A method of treating a mycobacterial infection, comprising the step of administering a therapeutically effective amount of a compound of paragraph 30 to a patient in need thereof.

41. The method of paragraph 40, wherein the mycobacterial infection is caused by *Mycobacterium tuberculosis, Mycobacterium avium, Mycobacterium kansasii, Mycobacterium abscessus* or *Mycobacterium chelonae*.

42. The method of paragraph 40, wherein the mycobacterial infection is caused by *Mycobacterium tuberculosis*.

It is to be understood that the invention is not limited to the particular embodiments of the invention described above, as variations of the particular embodiments may be made and still fall within the scope of the appended claims.

What is claimed is:

1. A compound of formula (I):

$$\left( (R_1)_p \underset{R_2}{\overset{X}{\underset{Y}{\bigcirc}}} -B^-F_3 \right)_q (M^{q+}),$$ (I)

wherein:
X and Y are each N;
M is Ca, Cs, K, Li, Mg, Na or tetraalkyl ammonium ion $(R_3)_4N^+$;
$R_1$ is, individually in each occurrence, hydrogen, halogen, alkoxy, halo-alkoxy, lower alkyl, halo-lower alkyl, CN, —(CH$_2$)$_t$CN, —NR$_3$R$_4$, cycloalkyl, or heterocycloalkyl, wherein said heterocycloalkyl is a 4 to 6-membered monocyclic ring having one or two ring carbons replaced by nitrogen;
$R_2$ is hydrogen, halogen, alkoxy, halo-alkoxy, lower alkyl, halo-lower alkyl, CN, —(CH$_2$)$_t$CN, —NR$_3$R$_4$, cycloalkyl, or heterocycloalkyl, wherein said heterocycloalkyl is a 4 to 6-membered monocyclic ring having one or two ring carbons replaced by nitrogen;
$R_3$ and $R_4$, independently of each other, are hydrogen or lower alkyl;
n is 2;
p is 1 or 2;
q is 1 or 2; and
t is 1, 2, 3 or 4.

2. The compound according to claim 1, wherein M is K, Li or Na.

3. The compound according to claim 1, wherein $R_1$ is, individually in each occurrence, hydrogen, halogen, alkoxy, halo-alkoxy, lower alkyl or halo-lower alkyl.

4. The compound according to claim 1, wherein $R_1$ is, individually in each occurrence, —CH$_2$CN, —NR$_3$R$_4$ or cyano.

5. The compound according to claim 1, wherein $R_1$ is, individually in each occurrence, cycloalkyl or heterocycloalkyl.

6. The compound according to claim 1, wherein $R_2$ is hydrogen or halogen.

7. The compound according to claim 1, wherein $R_2$ is alkoxy, halo-alkoxy, lower alkyl or halo-lower alkyl.

8. The compound according to claim 1, wherein p is 1.

9. The compound according to claim 1, wherein q is 1.

10. A compound, wherein said compound is:

wherein M is Ca, Cs, K, Li, Mg, Na or tetraalkyl ammonium ion $(R_3)_4N^+$.

11. A compound, wherein said compound is

12. A pharmaceutical composition, comprising a compound of Formula I according to claim 1 and one or more pharmaceutically acceptable carriers and/or additives.

13. The pharmaceutical composition, according to claim 12, further comprising one or more additional anti-infective agents.

14. The pharmaceutical composition according to claim 13, wherein said additional anti-infective agent is rifampicin, rifabutin, rifapentene, isoniazid, ethambutol, kanamycin, amikacin, capreomycin, clofazimine, cycloserine, para-aminosalicylic acid, linezolid, sutezolid, bedaquiline, delamanid, pretomanid, moxifloxacin or levofloxacin, or combinations thereof.

15. A compound of formula (II):

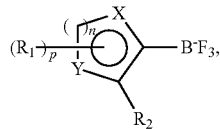

(II)

wherein:
X and Y are each N;
$R_1$ is $[(R_3)_3N^+]$— or $[(R_3)_3N^+(CH_2)_s]$—;
$R_2$ is hydrogen, halogen, alkoxy, halo-alkoxy, lower alkyl or halo-lower alkyl;
each $R_3$ is, independently, lower alkyl;
n is 2;
p is 1 or 2; and
s is 1, 2, 3, 4, 5 or 6.

16. The compound according to claim 15, wherein $R_1$ is:

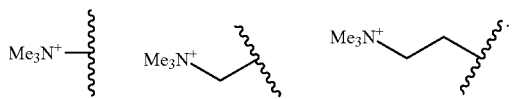

17. A compound, having formula (IIa):

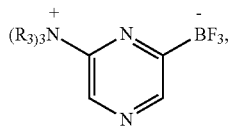

(IIa)

wherein each $R_3$ is, independently, methyl, ethyl, propyl, or isopropyl.

18. A compound, having formula (IIc):

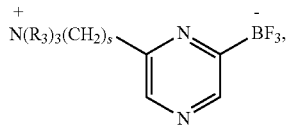

(IIc)

wherein:
each $R_3$ is, independently, methyl, ethyl, propyl, or isopropyl; and
s is 1, 2, 3 or 4.

19. A pharmaceutical composition comprising a compound of claim 15 and one or more pharmaceutically acceptable carriers and/or additives.

20. The pharmaceutical composition according to claim 19, further comprising one or more additional anti-infective agents.

* * * * *